United States Patent
Mager et al.

(10) Patent No.: US 10,317,392 B2
(45) Date of Patent: Jun. 11, 2019

(54) FORMATION AND CALIBRATION OF NANOPORE SEQUENCING CELLS

(71) Applicant: Roche Sequencing Solutions, Inc., Pleasanton, CA (US)

(72) Inventors: Morgan Mager, Sunnyvale, CA (US); John Mannion, Mountain View, CA (US)

(73) Assignee: Roche Sequencing Solutions, Inc., Pleasanton, CA (US)

( * ) Notice: Subject to any disclaimer, the term of this patent is extended or adjusted under 35 U.S.C. 154(b) by 31 days.

(21) Appl. No.: 15/632,190

(22) Filed: Jun. 23, 2017

(65) Prior Publication Data

US 2017/0370903 A1    Dec. 28, 2017

Related U.S. Application Data

(60) Provisional application No. 62/354,074, filed on Jun. 23, 2016.

(51) Int. Cl.
| | | |
|---|---|---|
| *G01N 33/487* | (2006.01) | |
| *C12Q 1/6869* | (2018.01) | |
| *C12Q 1/6874* | (2018.01) | |
| *G01N 27/447* | (2006.01) | |
| *G01N 27/327* | (2006.01) | |
| *G06F 19/22* | (2011.01) | |
| *B82Y 5/00* | (2011.01) | |
| *B82Y 15/00* | (2011.01) | |
| *G01N 27/416* | (2006.01) | |

(52) U.S. Cl.
CPC ..... *G01N 33/48721* (2013.01); *C12Q 1/6869* (2013.01); *C12Q 1/6874* (2013.01); *G01N 27/3278* (2013.01); *G01N 27/44791* (2013.01); *G06F 19/22* (2013.01); *B82Y 5/00* (2013.01); *B82Y 15/00* (2013.01); *C12Q 2563/116* (2013.01); *C12Q 2565/631* (2013.01); *G01N 27/4163* (2013.01)

(58) Field of Classification Search
CPC .................. G01N 33/48721; C12Q 1/6869
See application file for complete search history.

(56) References Cited

U.S. PATENT DOCUMENTS

| | | |
|---|---|---|
| 5,733,729 A | 3/1998 | Lipshutz et al. |
| 5,853,979 A | 12/1998 | Green et al. |
| 6,066,454 A | 5/2000 | Lipshutz et al. |
| 6,228,593 B1 | 5/2001 | Lipshutz et al. |
| 6,546,340 B2 | 4/2003 | Lipshutz et al. |
| 6,957,149 B2 | 10/2005 | Lipshutz et al. |
| 7,039,238 B2 | 5/2006 | Sonmez et al. |
| 7,133,781 B2 | 11/2006 | Toll et al. |
| 7,617,054 B2 | 11/2009 | Sayer et al. |
| 8,126,235 B2 | 2/2012 | Shi et al. |
| 8,182,993 B2 | 5/2012 | Tomaney et al. |
| 8,200,648 B2 | 6/2012 | Boiman et al. |
| 8,370,079 B2 | 2/2013 | Sorenson et al. |
| 8,428,886 B2 | 4/2013 | Wong et al. |
| 8,452,546 B1 * | 5/2013 | Lathrop ............... G06F 19/16 435/6.1 |
| 8,645,343 B2 | 2/2014 | Wong et al. |
| 8,703,422 B2 | 4/2014 | Tomaney et al. |
| 9,165,109 B2 | 10/2015 | Chaisson |
| 9,175,343 B2 | 11/2015 | Tomaney et al. |
| 9,194,838 B2 | 11/2015 | Taniguchi et al. |
| 9,218,451 B2 | 12/2015 | Wong et al. |
| 9,395,353 B2 | 7/2016 | Gu et al. |
| 9,546,400 B2 | 1/2017 | Turner et al. |
| 9,574,228 B2 | 2/2017 | Gu et al. |
| 9,689,033 B2 * | 6/2017 | Stava ............... C12Q 1/6869 |
| 2009/0012766 A1 | 1/2009 | Miyake et al. |
| 2010/0122907 A1 | 5/2010 | Stanford et al. |
| 2012/0173159 A1 | 7/2012 | Davey et al. |
| 2013/0060482 A1 | 3/2013 | Sikora et al. |
| 2013/0090860 A1 | 4/2013 | Sikora et al. |
| 2013/0217006 A1 | 8/2013 | Sorenson et al. |
| 2014/0134616 A1 | 5/2014 | Davis et al. |
| 2015/0111759 A1 | 4/2015 | Ju et al. |
| 2015/0119259 A1 | 4/2015 | Ju et al. |
| 2015/0169824 A1 | 6/2015 | Kermani et al. |
| 2015/0193431 A1 | 7/2015 | Stoytchev et al. |
| 2015/0347675 A1 * | 12/2015 | Schuller ............... G06F 19/22 702/19 |
| 2016/0097093 A1 | 4/2016 | Tomaney et al. |
| 2016/0138101 A1 | 5/2016 | Taniguchi et al. |
| 2016/0162634 A1 | 6/2016 | Reid et al. |
| 2017/0091427 A1 | 3/2017 | Massingham |
| 2017/0096703 A1 | 4/2017 | Dolan et al. |
| 2017/0154036 A9 | 6/2017 | Stoytchev et al. |
| 2017/0219557 A1 | 8/2017 | Reid et al. |

FOREIGN PATENT DOCUMENTS

| | | |
|---|---|---|
| EP | 0835442 B1 | 3/1999 |
| EP | 2758545 B1 | 7/2017 |

(Continued)

OTHER PUBLICATIONS

Denison, T.A.; "Chapter 5. Picoammeter 2: demodulating differentiator". *The Development of a Nanoscale Coulter Counter for Rapid Genetic Sequence Recognition*; Jul. 1, 2000; pp. 151-185.

(Continued)

*Primary Examiner* — Narayan K Bhat
(74) *Attorney, Agent, or Firm* — Kilpatrick Townsend & Stockton LLP

(57) ABSTRACT

Improved multi-cell nanopore-based sequencing chips and methods can employ formation, characterization, calibration, and/or normalization techniques. For example, various methods may include one or more steps of performing physical checks of cell circuitry, forming and characterizing a lipid layer on the cells, performing a zero point calibration of the cells, forming and characterizing nanopores on the lipid layers of each cell, performing a sequencing operation to accumulate sequencing signals from the cells, normalizing those sequencing signals, and determining bases based on the normalized sequencing signals.

21 Claims, 20 Drawing Sheets

(56) References Cited

FOREIGN PATENT DOCUMENTS

| WO | 2013/041878 A1 | | 3/2013 |
|---|---|---|---|
| WO | 2015/187670 A2 | | 12/2015 |
| WO | WO 2016/059427 | * | 4/2016 |
| WO | 2016/073318 A1 | | 5/2016 |

OTHER PUBLICATIONS

Faragher, R.; "Understanding the Basis of the Kalman Filter Via a Simple and Intuitive Derivation"; *IEEE Signal Processing Magazine*; Sep. 2012, pp. 128-132.

Gu, Z.; "Accurate Data Process for Analyzing Nanopore Data"; *Biophysical Journal*; vol. 110, No. 3; Mar. 1, 2016; 1 page.

Harrer, S. et al.; "Label-free screening of single biomolecules through resistive pulse sensing technology for prevision medicine applications"; *Nanotechnology*; vol. 26, No. 18; Apr. 15, 2015; 19 pages.

Timp, W. et al.; "DNA Base-Calling from a Nanopore Using a Viterbi Algorithm"; *Biophysical Journal*; vol. 102, No. 10; May 1, 2012; pp. 37-39.

Welch, G. et al.; "An Introduction to the Kalman Filter"; UNC-Chapel Hill, TR 95-041; Jul. 24, 2006; 16 pages.

Partial European Search Report for PCT Application PCT/US2017/039118 dated Sep. 12, 2017; 18 pages.

* cited by examiner

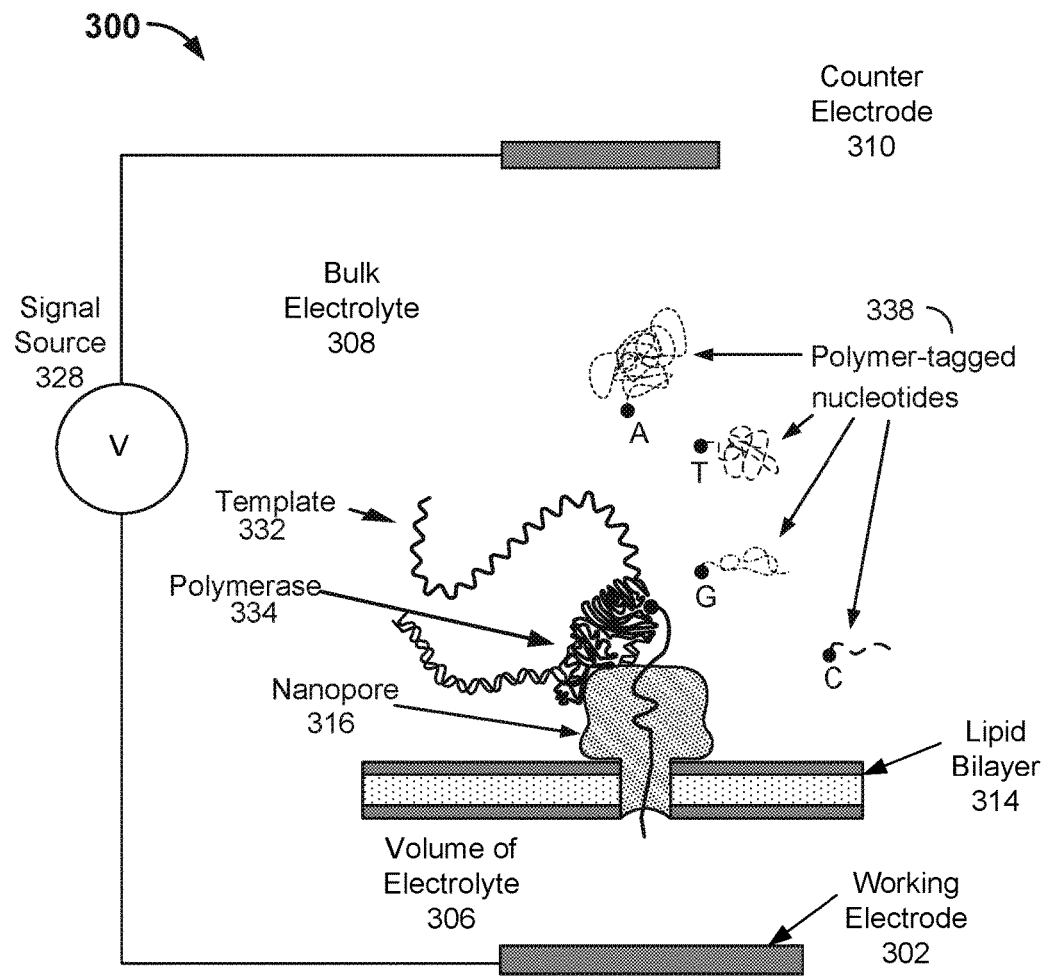
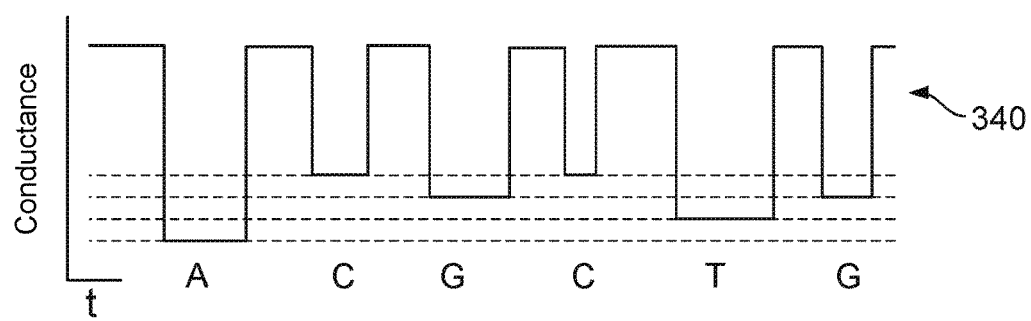
FIG. 3

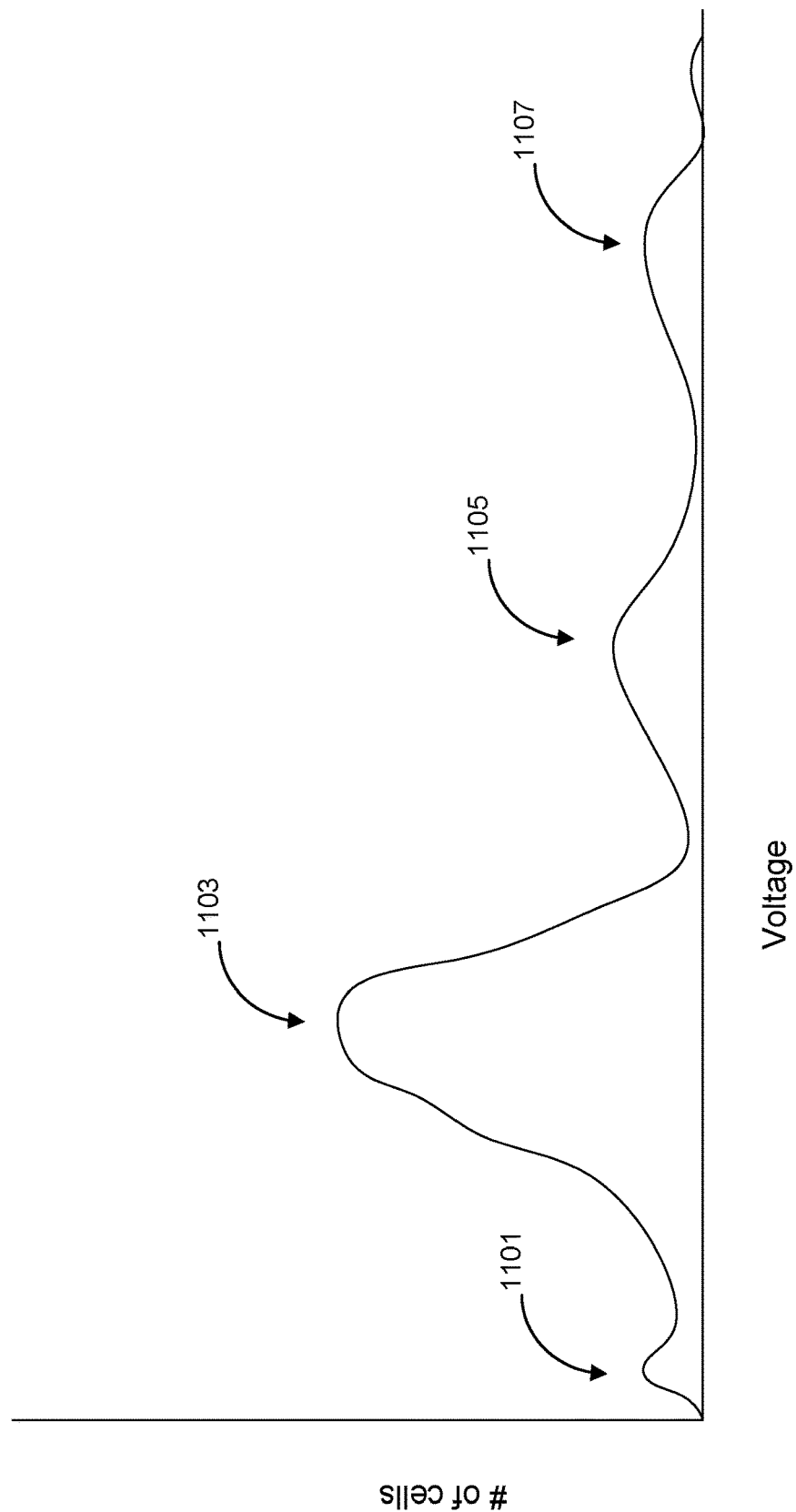

FORMATION AND CALIBRATION OF NANOPORE SEQUENCING CELLS

CROSS-REFERENCES TO RELATED APPLICATIONS

This application claims priority to U.S. Provisional Patent Application 62/354,074 filed Jun. 23, 2016, the disclosure of which is incorporated by reference in its entirety for all purposes.

BACKGROUND

Nanopore membrane devices having pore sizes on the order of one nanometer in internal diameter have shown promise in rapid nucleotide sequencing. When a voltage potential is applied across a nanopore immersed in a conducting fluid, a small ion current attributed to the conduction of ions across the nanopore can exist. The size of the current is sensitive to the pore size and which molecule in the nanopore. The molecule can be a particular tag attached to a particular nucleotide, thereby allowing detection of a nucleotide at a particular position of a nucleic acid. A voltage in a circuit including the nanopore can be measured (e.g., at an integrating capacitor) as a way of measuring the resistance of the molecule, thereby allowing detection of which molecule is in the nanopore.

A nanopore based sequencing chip may be used for DNA sequencing. A nanopore based sequencing chip can incorporate a large number of sensor cells configured as an array. For example, an array of one million cells may include 1000 rows by 1000 columns of cells.

The voltages that are measured can vary from chip to chip and from cell to cell of a same chip due to manufacturing variability. Therefore, it can be difficult to determine the correct molecule, which may be or correspond to the correct nucleotide in a particular nucleic acid or other polymer in a cell. In addition, other time dependent non-idealities in the measured voltages can lead to inaccuracies. And, because these circuits employ biochemical circuit elements, e.g., lipid bilayers, nanopores, etc., the variability in the electrical characteristics can be much higher than for traditional semiconductor circuits.

Accordingly, improved formation, characterization, calibration, and normalization techniques are desired to improve the accuracy and stability of sequencing processes.

BRIEF SUMMARY

Various embodiments provide techniques and systems related to the formation and calibration of nanopore sequencing cells and also to the normalization of output signals from cells of a multi-cell nanopore-based sequencing chip.

An improved multi-cell nanopore-based sequencing chip may be built by employing various embodiment for the formation, characterization, calibration, and/or normalization techniques disclosed herein. For example, embodiments can include performing physical checks of cell circuitry, forming and characterizing a lipid layer on the cells, performing a zero point calibration of the cells, forming and characterizing nanopores on the lipid layers of each cell, performing a sequencing operation to accumulate sequencing signals from the cells, normalizing those sequencing signals, and determining bases based on the normalized sequencing signals.

According to one embodiment, the number of nanopores present in each cell can be characterized. For example, a diagnostic voltage level can be measured and monitored for each cell. Processing techniques disclosed herein provide for one or more ways to characterize the state of the lipid bilayer (e.g., how many nanopores are present in the bilayer, if any) based on the measured voltage level. The cells of a sequencing chip with undesirable pore configuration can be removed or modified, thereby resulting in improved base detection capabilities, e.g., by removing errors and/or spurious signals produced by cells with undesirable pore configuration.

According to another embodiment, cells of the multi-cell nanopore-based sequencing chip may be calibrated to provide consistent output voltages. For example, cell-specific voltage offsets (also referred to herein as zero point voltages) can be measured and compensated. Measurements can be made on a one-time basis or may be made multiple times over the life of a cell as properties of the cell change over time.

According to another embodiment, methods and systems are directed to the normalization of sequencing signals that are output from cells of a multi-cell nanopore-based sequencing chip. For example, each cell may be modelled as a certain type of analog circuit, with the cell's elements (e.g., electrodes, lipid bilayer, nanopore, etc.) being included in the model as discrete elements, e.g., as resistive and/or capacitive elements. The model may then be employed to estimate or predict one or more normalization factors that can be used to correct for a number of cell-specific non-idealities in a cell's respective sequencing signal, e.g., gain drift and offset shift of sequencing signals may be compensated for using one or more methods disclosed herein. As another example, voltage measurements from one portion of an alternating signal (e.g., a positive voltage relative to a reference voltage) can be used to normalize voltage measurements made during the opposite portion, e.g., when the nanopores are in threaded states and minimal open channel voltages are available.

Other embodiments are directed to systems and computer readable media associated with methods described herein.

A better understanding of the nature and advantages of embodiments of the present invention may be gained with reference to the following detailed description and the accompanying drawings.

BRIEF DESCRIPTION OF THE DRAWINGS

FIG. 3 illustrates an embodiment of a nanopore cell performing nucleotide sequencing using a nanopore-based sequencing-by-synthesis (Nano-SBS) technique.

FIG. 11 shows a kernel density estimate (KDE) of voltage values for different cells according to certain embodiments.

TERMS

Figure 1:
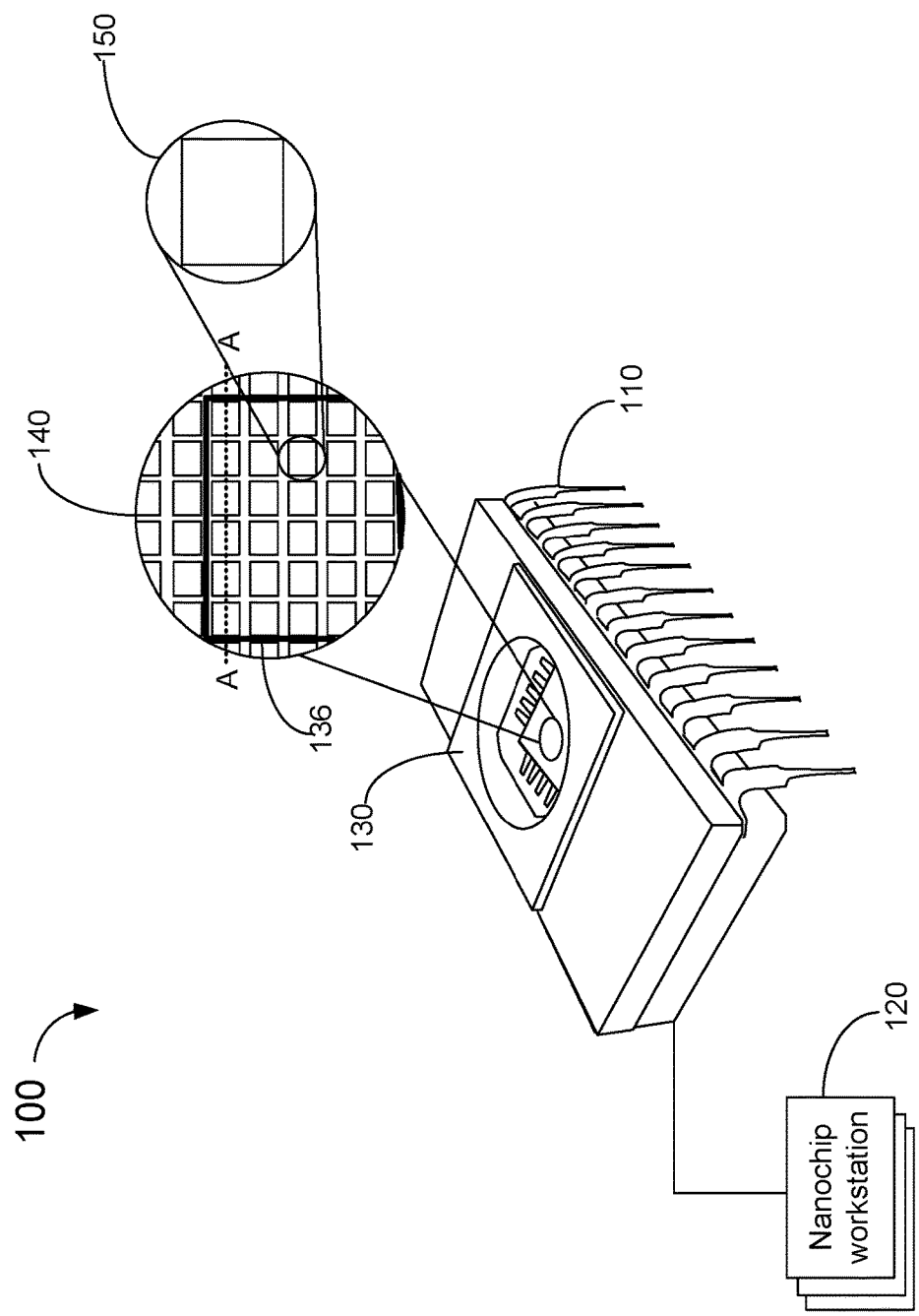
FIG. 1 is a top view of an embodiment of a nanopore sensor chip having an array of nanopore cells.

Unless defined otherwise, technical and scientific terms used herein have the same meaning as commonly understood by a person of ordinary skill in the art. Methods, devices, and materials similar or equivalent to those described herein can be used in the practice of disclosed techniques. The following terms are provided to facilitate understanding of certain terms used frequently and are not meant to limit the scope of the present disclosure. Abbreviations used herein have their conventional meaning within the chemical and biological arts.

"Nucleic acid" may refer to deoxyribonucleotides or ribonucleotides and polymers thereof in either single- or double-stranded form. The term may encompass nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs may include, without limitation, phosphorothioates, phosphoramidites, methyl phosphonates, chiral-methyl phosphonates, 2-O-methyl ribonucleotides, peptide-nucleic acids (PNAs). Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); Rossolini et al., *Mol. Cell. Probes* 8:91-98 (1994)). The term nucleic acid may be used interchangeably with gene, cDNA, mRNA, oligonucleotide, and polynucleotide.

The term "template" may refer to a single stranded nucleic acid molecule that is copied into a complementary strand of DNA nucleotides for DNA synthesis. In some cases, a template may refer to the sequence of DNA that is copied during the synthesis of mRNA.

The term "primer" may refer to a short nucleic acid sequence that provides a starting point for DNA synthesis. Enzymes that catalyze the DNA synthesis, such as DNA polymerases, can add new nucleotides to a primer for DNA replication.

"Polymerase" refers to an enzyme that performs template-directed synthesis of polynucleotides. The term encompasses both a full length polypeptide and a domain that has polymerase activity. DNA polymerases are well-known to those skilled in the art, and include but are not limited to DNA polymerases isolated or derived from *Pyrococcus furiosus*, *Thermococcus litoralis*, and *Thermotoga maritime*, or modified versions thereof. They include both DNA-dependent polymerases and RNA-dependent polymerases such as reverse transcriptase. At least five families of DNA-dependent DNA polymerases are known, although most fall into families A, B and C. There is little or no sequence similarity among the various families. Most family A polymerases are single chain proteins that can contain multiple enzymatic functions including polymerase, 3' to 5' exonuclease activity and 5' to 3' exonuclease activity. Family B polymerases typically have a single catalytic domain with polymerase and 3' to 5' exonuclease activity, as well as accessory factors. Family C polymerases are typically multi-subunit proteins with polymerizing and 3' to 5' exonuclease activity. In *E. coli*, three types of DNA polymerases have been found, DNA polymerases I (family A), II (family B), and III (family C). In eukaryotic cells, three different family B polymerases, DNA polymerases $\alpha$, $\delta$, and $\epsilon$, are implicated in nuclear replication, and a family A polymerase, polymerase $\gamma$, is used for mitochondrial DNA replication. Other types of DNA polymerases include phage polymerases. Similarly, RNA polymerases typically include eukaryotic RNA polymerases I, II, and III, and bacterial RNA polymerases as well as phage and viral polymerases. RNA polymerases can be DNA-dependent and RNA-dependent.

"Nanopore" refers to a pore, channel or passage formed or otherwise provided in a membrane. A membrane can be an organic membrane, such as a lipid bilayer, or a synthetic membrane, such as a membrane formed of a polymeric material. The nanopore can be disposed adjacent or in proximity to a sensing circuit or an electrode coupled to a sensing circuit, such as, for example, a complementary metal oxide semiconductor (CMOS) or field effect transistor (FET) circuit. In some examples, a nanopore has a characteristic width or diameter on the order of 0.1 nanometers (nm) to about 1000 nm. Some nanopores are proteins.

"Nucleotide," in addition to referring to the naturally occurring ribonucleotide or deoxyribonucleotide monomers, can be understood to refer to related structural variants thereof, including derivatives and analogs, that are functionally equivalent with respect to the particular context in which the nucleotide is being used (e.g., hybridization to a complementary base), unless the context clearly indicates otherwise.

"Tag" refers to a detectable moiety that can be atoms or molecules, or a collection of atoms or molecules. A tag can provide an optical, electrochemical, magnetic, or electrostatic (e.g., inductive, capacitive) signature, which signature may be detected with the aid of a nanopore. Typically, when a nucleotide is attached to the tag it is called a "Tagged Nucleotide." The tag can be attached to the nucleotide via the phosphate moiety.

As used herein, the term "bright period" may generally refer to the time period when a tag of a tagged nucleotide is forced into a nanopore by an electric field applied through an AC signal. The term "dark period" may generally refer to the time period when a tag of a tagged nucleotide is pushed out of the nanopore by the electric field applied through the AC signal. An AC cycle may include the bright period and the dark period. In different embodiments, the polarity of the voltage signal applied to a nanopore cell to put the nanopore cell into the bright period (or the dark period) may be different.

As used herein, the term "signal value" may refer to a value of the sequencing signal output from a sequencing cell. According to certain embodiments, the sequencing signal may be an electrical signal that is measured and/or output from a point in a circuit of one or more sequencing cells e.g., the signal value may be (or represent) a voltage or a current. The signal value may represent the results of a direct measurement of voltage and/or current and/or may represent an indirect measurement, e.g., the signal value may be a measured duration of time for which it takes a voltage or current to reach a specified value. A signal value may represent any measurable quantity that correlates with the resistivity of a nanopore and from which the resistivity and/or conductance of the nanopore (threaded and/or unthreaded) may be derived.

DETAILED DESCRIPTION

According to certain embodiments, techniques and systems disclosed herein relate to cell-by-cell determinations of the number of pores that perforate a lipid bi-layer within each cell, to cell-by-cell calibration techniques, and to sequencing signal normalization methods that can be applied on a cell-by-cell basis to the output signals of individual cells of a multi-cell nanopore-based sequencing chip.

In various embodiments, a data sampling and conversion circuit associated with nanopore cells in a column can sequentially sample and convert output voltage signals from each nanopore cell in the column, as part of identifying a tag (e.g., attached to a nucleotide) and consequently a nucleotide being incorporated into a nucleic acid. The stability and accuracy of the output voltage signal from each nanopore cell is of critical importance to the chip's overall ability to accurately and quickly sequence a DNA molecule under investigation. A number of issues can affect the stability and accuracy of the voltage signal, including the gain of voltage measurements for a cell can drift over time, the baseline voltage of a cell can shift over time, and various DC offsets can develop within a cell as stray charge is injected into the cell's capacitive elements.

To address these issues, adaptable signal normalization techniques (e.g., hybrid-online normalization)can perform point-by-point normalization of measurements, e.g., of a voltage signal, which can be done as the measurement is being acquired. The normalized voltages can provide more consistent values for each tag being detected, and thus can better distinguish and identify different bases of the DNA molecule. Offline calibration techniques are also disclosed that can provide for a way to detect and correct for certain DC offsets in the baseline voltage level for individual cells.

In addition, the properties of individual cells can vary cell-by-cell due to manufacturing non-uniformities. While it is preferable to have a single nanopore per cell, it is possible that during the poration step (i.e., the process of inserting, for example a protein nanopore transmembrane molecular complexes (PNTMC) into a cell's lipid bilayer), some cells end up having zero pores and some may have more than one. This can make it difficult to interpret the output signals of the sequencing chip, which itself can contain thousands, if not millions of cells. Some embodiments can characterize the number of pores present in cells of a multi-cell nanopore-based sequencing chip, e.g., via histogram-based measurement techniques.

I. Nanopore Based Sequencing Chip

FIG. 1 is a top view of an embodiment of a nanopore sensor chip 100 having an array 140 of nanopore cells 150. Each nanopore cell 150 includes a control circuit integrated on a silicon substrate of nanopore sensor chip 100. In some embodiments, side walls 136 may be included in array 140 to separate groups of nanopore cells 150 so that each group may receive a different sample for characterization. Each nanopore cell may be used to sequence a nucleic acid. In some embodiments, nanopore sensor chip 100 may include a cover plate 130. In some embodiments, nanopore sensor chip 100 may also include a plurality of pins 110 for interfacing with other circuits, such as a computer processor.

In some embodiments, nanopore sensor chip 100 may include multiple chips in a same package, such as, for example, a Multi-Chip Module (MCM) or System-in-Package (SiP). The chips may include, for example, a memory, a processor, a field-programmable gate array (FPGA), an application-specific integrated circuit (ASIC), data converters, a high-speed I/O interface, etc.

In some embodiments, nanopore sensor chip 100 may be coupled to (e.g., docked to) a nanochip workstation 120, which may include various components for carrying out (e.g., automatically carrying out) various embodiments of the processes disclosed herein, including, for example, analyte delivery mechanisms, such as pipettes for delivering lipid suspension or other membrane structure suspension, analyte solution, and/or other liquids, suspension or solids, robotic arms, computer processor, and/or memory. A plurality of polynucleotides may be detected on array 140 of nanopore cells 150. In some embodiments, each nanopore cell 150 can be individually addressable.

II. Nanopore Sequencing Cell

Nanopore cells 150 in nanopore sensor chip 100 may be implemented in many different ways. For example, in some embodiments, tags of different sizes and/or chemical structures may be attached to different nucleotides in a nucleic acid molecule to be sequenced. In some embodiments, a complementary strand to a template of the nucleic acid molecule to be sequenced may be synthesized by hybridizing differently polymer-tagged nucleotides with the template. In some implementations, the nucleic acid molecule and the attached tags may both move through the nanopore, and an ion current passing through the nanopore may indicate the nucleotide that is in the nanopore because of the particular size and/or structure of the tag attached to the nucleotide. In some implementations, only the tags may be moved into the nanopore. There may also be many different ways to detect the different tags in the nanopores.

A. Nanopore Sequencing Cell Structure

Figure 2:
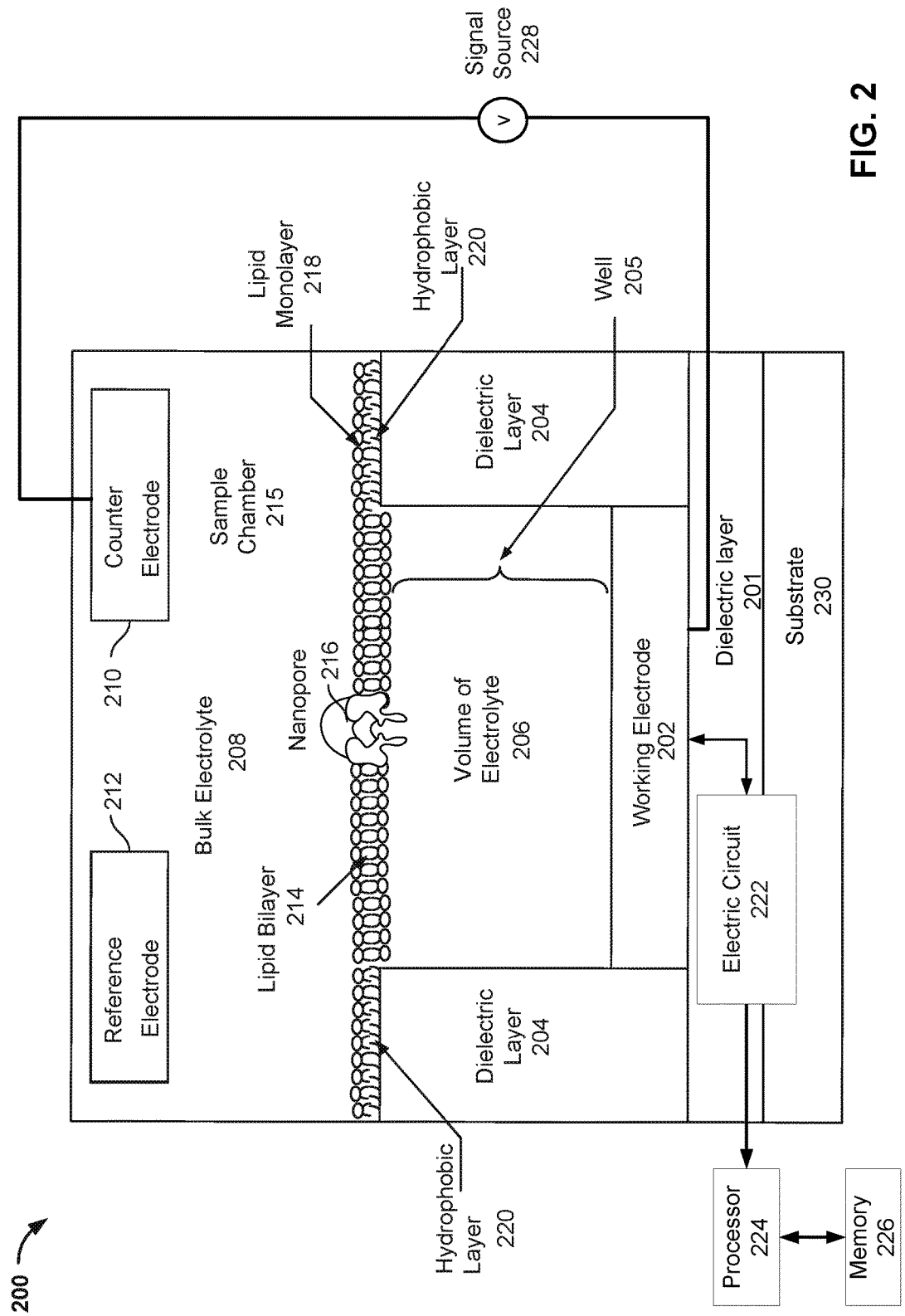
FIG. 2 illustrates an embodiment of a nanopore cell in a nanopore sensor chip that can be used to characterize a polynucleotide or a polypeptide.

FIG. 2 illustrates an embodiment of an example nanopore cell 200 in a nanopore sensor chip, such as nanopore cell 150 in nanopore sensor chip 100 of FIG. 1, that can be used to characterize a polynucleotide or a polypeptide. Nanopore cell 200 may include a well 205 formed of dielectric layers 201 and 204; a membrane, such as a lipid bilayer 214 formed over well 205; and a sample chamber 215 on lipid bilayer 214 and separated from well 205 by lipid bilayer 214. Well 205 may contain a volume of electrolyte 206, and sample chamber 215 may hold bulk electrolyte 208 containing a nanopore, e.g., a soluble protein nanopore transmembrane molecular complexes (PNTMC), and the analyte of interest (e.g., a nucleic acid molecule to be sequenced).

Nanopore cell 200 may include a working electrode 202 at the bottom of well 205 and a counter electrode 210 disposed in sample chamber 215. A signal source 228 may apply a voltage signal between working electrode 202 and counter electrode 210. A single nanopore (e.g., a PNTMC) may be inserted into lipid bilayer 214 by an electroporation process caused by the voltage signal, thereby forming a nanopore 216 in lipid bilayer 214. The individual membranes (e.g., lipid bilayers 214 or other membrane structures) in the array may be neither chemically nor electrically connected to each other. Thus, each nanopore cell in the array may be an independent sequencing machine, producing data unique to the single polymer molecule associated with the nanopore that operates on the analyte of interest and modulates the ionic current through the otherwise impermeable lipid bilayer.

As shown in FIG. 2, nanopore cell 200 may be formed on a substrate 230, such as a silicon substrate. Dielectric layer 201 may be formed on substrate 230. Dielectric material used to form dielectric layer 201 may include, for example, glass, oxides, nitrides, and the like. An electric circuit 222 for controlling electrical stimulation and for processing the signal detected from nanopore cell 200 may be formed on substrate 230 and/or within dielectric layer 201. For example, a plurality of patterned metal layers (e.g., metal 1 to metal 6) may be formed in dielectric layer 201, and a plurality of active devices (e.g., transistors) may be fabricated on substrate 230. In some embodiments, signal source 228 is included as a part of electric circuit 222. Electric circuit 222 may include, for example, amplifiers, integrators, analog-to-digital converters, noise filters, feedback control logic, and/or various other components. Electric circuit 222 may be further coupled to a processor 224 that is coupled to a memory 226, where processor 224 can analyze the sequencing data to determine sequences of the polymer molecules that have been sequenced in the array.

Working electrode 202 may be formed on dielectric layer 201, and may form at least a part of the bottom of well 205. In some embodiments, working electrode 202 is a metal electrode. For non-faradaic conduction, working electrode 202 may be made of metals or other materials that are resistant to corrosion and oxidation, such as, for example, platinum, gold, titanium nitride, and graphite. For example, working electrode 202 may be a platinum electrode with electroplated platinum. In another example, working electrode 202 may be a titanium nitride (TiN) working electrode. Working electrode 202 may be porous, thereby increasing its surface area and a resulting capacitance associated with working electrode 202. Because the working electrode of a nanopore cell may be independent from the working electrode of another nanopore cell, the working electrode may be referred to as cell electrode in this disclosure.

Dielectric layer 204 may be formed above dielectric layer 201. Dielectric layer 204 forms the walls surrounding well 205. Dielectric material used to form dielectric layer 204 may include, for example, glass, oxide, silicon mononitride (SiN), polyimide, or other suitable hydrophobic insulating material. The top surface of dielectric layer 204 may be silanized. The silanization may form a hydrophobic layer 220 above the top surface of dielectric layer 204. In some embodiments, hydrophobic layer 220 has a thickness of about 1.5 nanometer (nm).

Well 205 formed by the dielectric layer walls 204 includes volume of electrolyte 206 above working electrode 202. Volume of electrolyte 206 may be buffered and may include one or more of the following: lithium chloride (LiCl), sodium chloride (NaCl), potassium chloride (KCl), lithium glutamate, sodium glutamate, potassium glutamate, lithium acetate, sodium acetate, potassium acetate, calcium chloride ($CaCl_2$), strontium chloride ($SrCl_2$), manganese chloride ($MnCl_2$), and magnesium chloride ($MgCl_2$). In some embodiments, volume of electrolyte 206 has a thickness of about three microns ($\mu m$).

As also shown in FIG. 2, a membrane may be formed on top of dielectric layer 204 and span across well 205. In some embodiments, the membrane may include a lipid monolayer 218 formed on top of hydrophobic layer 220. As the membrane reaches the opening of well 205, lipid monolayer 208 may transition to lipid bilayer 214 that spans across the opening of well 205. The lipid bilayer may comprise or consist of phospholipid, for example, selected from diphytanoyl-phosphatidylcholine (DPhPC), 1,2-diphytanoyl-sn-glycero-3-phosphocholine, 1,2-Di-O-Phytanyl-sn-Glycero-3-phosphocholine (DoPhPC), palmitoyl-oleoyl-phosphatidylcholine (POPC), dioleoyl-phosphatidyl-methylester (DOPME), dipalmitoylphosphatidylcholine (DPPC), phosphatidylcholine, phosphatidylethanolamine, phosphatidylserine, phosphatidic acid, phosphatidylinositol, phosphatidylglycerol, sphingomyelin, 1,2-di-O-phytanyl-sn-glycerol; 1,2-dipalmitoyl-sn-glycero-3-phosphoethanolamine-N-[methoxy(polyethylene glycol)-350]; 1,2-dipalmitoyl-sn-glycero-3-phosphoethanolamine-N-[methoxy (polyethylene glycol)-550]; 1,2-dipalmitoyl-sn-glycero-3-phosphoethanolamine-N-[methoxy(polyethylene glycol)-750]; 1,2-dipalmitoyl-sn-glycero-3-phosphoethanolamine-N-[methoxy(polyethylene glycol)-1000]; 1,2-dipalmitoyl-sn-glycero-3-phosphoethanolamine-N-[methoxy (polyethylene glycol)-2000]; 1,2-dioleoyl-sn-glycero-3-phosphoethanolamine-N-lactosyl; GM1 Ganglioside, Lysophosphatidylcholine (LPC) or any combination thereof.

As shown, lipid bilayer 214 is embedded with a single nanopore 216, e.g., formed by a single PNTMC. As described above, nanopore 216 may be formed by inserting a single PNTMC into lipid bilayer 214 by electroporation. Nanopore 216 may be large enough for passing at least a portion of the analyte of interest and/or small ions (e.g., $Na^+$, $K^+$, $Ca^{2+}$, $Cl^-$) between the two sides of lipid bilayer 214.

Sample chamber 215 is over lipid bilayer 214, and can hold a solution of the analyte of interest for characterization. The solution may be an aqueous solution containing bulk electrolyte 208 and buffered to an optimum ion concentration and maintained at an optimum pH to keep the nanopore 216 open. Nanopore 216 crosses lipid bilayer 214 and provides the only path for ionic flow from bulk electrolyte 208 to working electrode 202. In addition to nanopores (e.g., PNTMCs) and the analyte of interest, bulk electrolyte 208 may further include one or more of the following: lithium chloride (LiCl), sodium chloride (NaCl), potassium chloride (KCl), lithium glutamate, sodium glutamate, potassium glutamate, lithium acetate, sodium acetate, potassium acetate, calcium chloride ($CaCl_2$), strontium chloride ($SrCl_2$), Manganese chloride ($MnCl_2$), and magnesium chloride ($MgCl_2$).

Counter electrode (CE) 210 may be an electrochemical potential sensor. In some embodiments, counter electrode 210 may be shared between a plurality of nanopore cells, and may therefore be referred to as a common electrode. In some cases, the common potential and the common electrode may be common to all nanopore cells, or at least all nanopore cells within a particular grouping. The common electrode can be configured to apply a common potential to the bulk electrolyte 208 in contact with the nanopore 216. Counter electrode 210 and working electrode 202 may be coupled to signal source 228 for providing electrical stimulus (e.g., voltage bias) across lipid bilayer 214, and may be used for sensing electrical characteristics of lipid bilayer 214 (e.g., resistance, capacitance, and ionic current flow). In some embodiments, nanopore cell 200 can also include a reference electrode 212.

In some embodiments, various checks can be made during creation of the nanopore cell as part of calibration. Once a nanopore cell is created, further calibration steps can be performed, e.g., to identify nanopore cells that are performing as desired (e.g., one nanopore in the cell). Such calibration checks can include physical checks, voltage calibration, open channel calibration, and identification of cells with a single nanopore.

B. Detection Signals of Nanopore Sequencing Cell

Nanopore cells in nanopore sensor chip, such as nanopore cells 150 in nanopore sensor chip 100, may enable parallel sequencing using a single molecule nanopore-based sequencing by synthesis (Nano-SBS) technique.

FIG. 3 illustrates an embodiment of a nanopore cell 300 performing nucleotide sequencing using the Nano-SBS technique. In the Nano-SBS technique, a template 332 to be sequenced (e.g., a nucleotide acid molecule or another analyte of interest) and a primer may be introduced into bulk electrolyte 308 in the sample chamber of nanopore cell 300. As examples, template 332 can be circular or linear. A nucleic acid primer may be hybridized to a portion of template 332 to which four differently polymer-tagged nucleotides 338 may be added.

In some embodiments, an enzyme (e.g., a polymerase 334, such as a DNA polymerase) may be associated with nanopore 316 for use in the synthesizing a complementary strand to template 332. For example, polymerase 334 may be covalently attached to nanopore 316. Polymerase 334 may catalyze the incorporation of nucleotides 338 onto the primer using a single stranded nucleic acid molecule as the template. Nucleotides 338 may comprise tag species ("tags") with the nucleotide being one of four different types: A, T, G, or C. When a tagged nucleotide is correctly complexed with polymerase 334, the tag may be pulled (loaded) into the nanopore by an electrical force, such as a force generated in the presence of an electric field generated by a voltage applied across lipid bilayer 314 and/or nanopore 316. The tail of the tag may be positioned in the barrel of nanopore 316. The tag held in the barrel of nanopore 316 may generate a unique ionic blockade signal 340 due to the tag's distinct chemical structure and/or size, thereby electronically identifying the added base to which the tag attaches.

As used herein, a "loaded" or "threaded" tag may be one that is positioned in and/or remains in or near the nanopore for an appreciable amount of time, e.g., 0.1 millisecond (ms) to 10000 ms. In some cases, a tag is loaded in the nanopore prior to being released from the nucleotide. In some instances, the probability of a loaded tag passing through (and/or being detected by) the nanopore after being released upon a nucleotide incorporation event is suitably high, e.g., 90% to 99%.

In some embodiments, before polymerase 334 is connected to nanopore 316, the conductance of nanopore 316 may be high, such as, for example, about 300 picosiemens (300 pS). As the tag is loaded in the nanopore, a unique conductance signal (e.g., signal 340) is generated due to the tag's distinct chemical structure and/or size. For example, the conductance of the nanopore can be about 60 pS, 80 pS, 100 pS, or 120 pS, each corresponding to one of the four types of tagged nucleotides. The polymerase may then undergo an isomerization and a transphosphorylation reaction to incorporate the nucleotide into the growing nucleic acid molecule and release the tag molecule.

In some cases, some of the tagged nucleotides may not match (complementary bases) with a current position of the nucleic acid molecule (template). The tagged nucleotides that are not base-paired with the nucleic acid molecule may also pass through the nanopore. These non-paired nucleotides can be rejected by the polymerase within a time scale that is shorter than the time scale for which correctly paired nucleotides remain associated with the polymerase. Tags bound to non-paired nucleotides may pass through the nanopore quickly, and be detected for a short period of time (e.g., less than 10 ms), while tags bounded to paired nucleotides can be loaded into the nanopore and detected for a long period of time (e.g., at least 10 ms). Therefore, non-paired nucleotides may be identified by a downstream processor based at least in part on the time for which the nucleotide is detected in the nanopore.

A conductance (or equivalently the resistance) of the nanopore including the loaded (threaded) tag can be measured via a current passing through the nanopore, thereby providing an identification of the tag species and thus the nucleotide at the current position. In some embodiments, a direct current (DC) signal can be applied to the nanopore cell (e.g., so that the direction at which the tag moves through the nanopore is not reversed). However, operating a nanopore sensor for long periods of time using a direct current can change the composition of the electrode, unbalance the ion concentrations across the nanopore, and have other undesirable effects that can affect the lifetime of the nanopore cell. Applying an alternating current (AC) waveform can reduce the electro-migration to avoid these undesirable effects and have certain advantages as described below. The nucleic acid sequencing methods described herein that utilize tagged nucleotides are fully compatible with applied AC voltages, and therefore an AC waveform can be used to achieve these advantages.

The ability to re-charge the electrode during the AC detection cycle can be advantageous when sacrificial electrodes, electrodes that change molecular character in the current-carrying reactions (e.g., electrodes comprising silver), or electrodes that change molecular character in current-carrying reactions are used. An electrode may deplete during a detection cycle when a direct current signal is used. The recharging can prevent the electrode from reaching a depletion limit, such as becoming fully depleted, which can be a problem when the electrodes are small (e.g., when the electrodes are small enough to provide an array of electrodes having at least 500 electrodes per square millimeter). Electrode lifetime in some cases scales with, and is at least partly dependent on, the width of the electrode.

Suitable conditions for measuring ionic currents passing through the nanopores are known in the art and examples are provided herein. The measurement may be carried out with a voltage applied across the membrane and pore. In some embodiments, the voltage used may range from −400 mV to +400 mV. The voltage used is preferably in a range having a lower limit selected from −400 mV, −300 mV, −200 mV, −150 mV, −100 mV, −50 mV, −20 mV, and 0 mV, and an upper limit independently selected from +10 mV, +20 mV, +50 mV, +100 mV, +150 mV, +200 mV, +300 mV, and +400 mV. The voltage used may be more preferably in the range of 100 mV to 240 mV and most preferably in the range of 160 mV to 240 mV. It is possible to increase discrimination between different nucleotides by a nanopore using an increased applied potential. Sequencing nucleic acids using AC waveforms and tagged nucleotides is described in US Patent Publication No. US 2014/0134616 entitled "Nucleic Acid Sequencing Using Tags," filed on Nov. 6, 2013, which is herein incorporated by reference in its entirety. In addition to the tagged nucleotides described in US 2014/0134616, sequencing can be performed using nucleotide analogs that lack a sugar or acyclic moiety, e.g., (S)-Glycerol nucleoside triphosphates (gNTPs) of the five common nucleobases: adenine, cytosine, guanine, uracil, and thymine (Horhota et al., Organic Letters, 8:5345-5347 [2006]).

C. Electric Circuit of Nanopore Sequencing Cell

Figure 4:
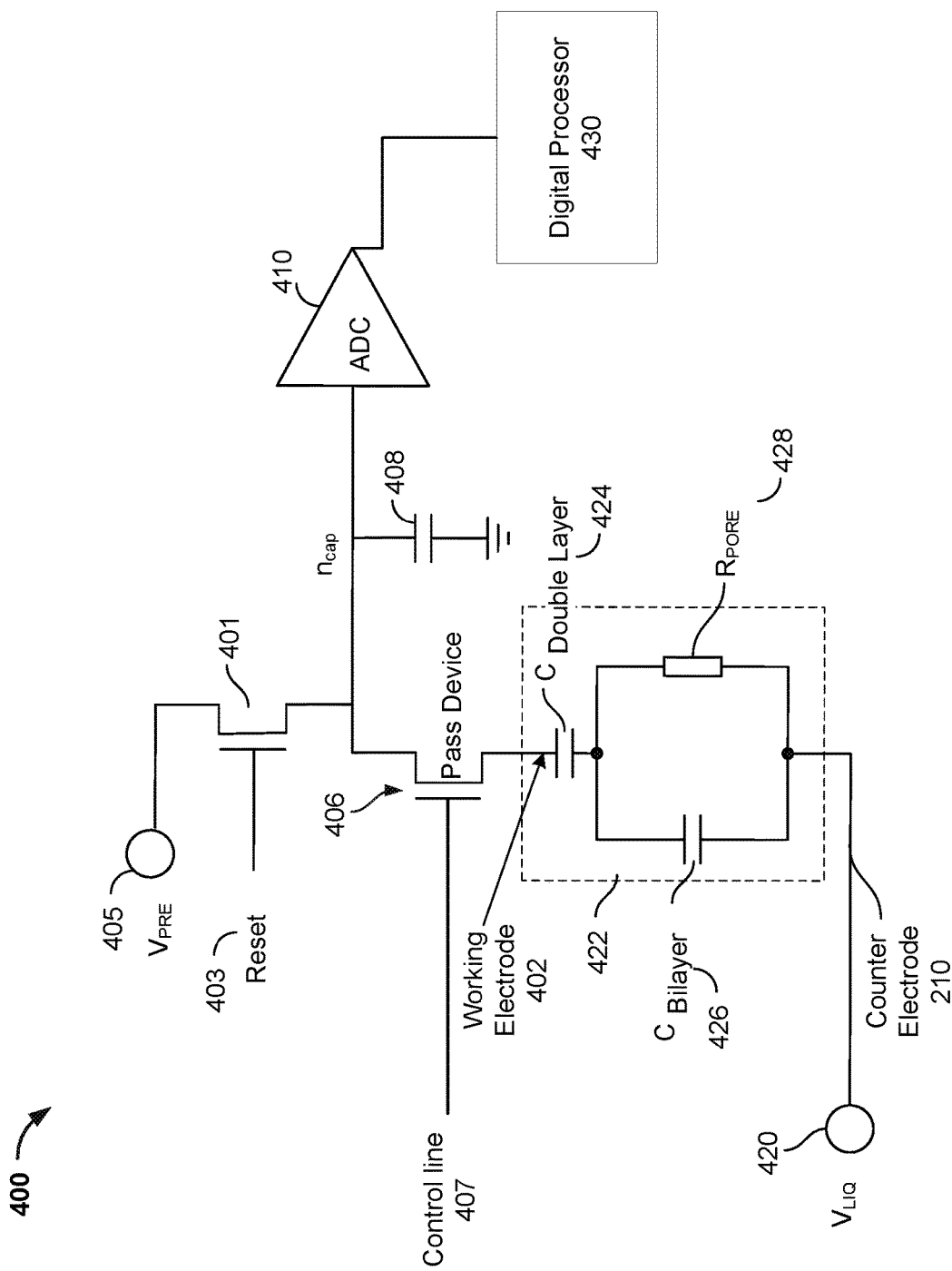
FIG. 4 illustrates an embodiment of an electric circuit in a nanopore cell.

FIG. 4 illustrates an embodiment of an electric circuit 400 (which may include portions of electric circuit 222 in FIG. 2) in a nanopore cell, such as nanopore cell 200. As described above, in some embodiments, electric circuit 400 includes a counter electrode 210 that may be shared between a plurality of nanopore cells or all nanopore cells in a nanopore sensor chip, and may therefore also be referred to as a common electrode. The common electrode can be configured to apply a common potential to the bulk electrolyte (e.g., bulk electrolyte 208) in contact with the lipid bilayer (e.g., lipid bilayer 214) in the nanopore cells by connecting to a voltage source $V_{LIQ}$ 420. In some embodiments, an AC non-Faradaic mode may be utilized to modulate voltage $V_{LIQ}$ with an AC signal (e.g., a square wave) and apply it to the bulk electrolyte in contact with the lipid bilayer in the nanopore cell. In some embodiments, $V_{LIQ}$ is a square wave with a magnitude of ±200-250 mV and a frequency between, for example, 25 and 400 Hz. The bulk electrolyte between counter electrode 210 and the lipid bilayer (e.g., lipid bilayer 214) may be modeled by a large capacitor (not shown), such as, for example, 100 µF or larger.

FIG. 4 also shows an electrical model 422 representing the electrical properties of a working electrode (e.g., working electrode 202) and the lipid bilayer (e.g., lipid bilayer 214). Electrical model 422 includes a capacitor 426 ($C_{Bilayer}$) that models a capacitance associated with the lipid bilayer and a resistor 428 ($R_{PORE}$) that models a variable resistance (also referred to herein as a resistive element) associated with the nanopore, which can change based on the presence of a particular tag in the nanopore. Electrical model 422 also includes a capacitor 424 having a double layer capacitance ($C_{Double\ Layer}$) and representing the electrical properties of working electrode 202 and well 205. Working electrode 202 may be configured to apply a distinct potential independent from the working electrodes in other nanopore cells.

Pass device 406 is a switch that can be used to connect or disconnect the lipid bilayer and the working electrode from electric circuit 400. Pass device 406 may be controlled by control line 407 to enable or disable a voltage stimulus to be applied across the lipid bilayer in the nanopore cell. Before lipids are deposited to form the lipid bilayer, the impedance between the pair of electrodes may be very low because the well of the nanopore cell is not sealed, and therefore pass device 406 may be kept open to avoid a short-circuit condition. Pass device 406 may be closed after lipid solvent has been deposited to the nanopore cell to seal the well of the nanopore cell.

Circuitry 400 may further include an on-chip integrating capacitor 408 ($n_{cap}$). Integrating capacitor 408 may be pre-charged by using a reset signal 403 to close switch 401, such that integrating capacitor 408 is connected to a voltage source $V_{PRE}$ 405. In some embodiments, voltage source $V_{PRE}$ 405 provides a constant reference voltage with a magnitude of, for example, 900 mV. When switch 401 is closed, integrating capacitor 408 may be pre-charged to a specified voltage level (or reference voltage) of voltage source $V_{PRE}$ 405.

After integrating capacitor 408 is pre-charged, reset signal 403 may be used to open switch 401 such that integrating capacitor 408 is disconnected from voltage source $V_{PRE}$ 405. At this point, depending on the level of voltage source $V_{LIQ}$, the potential of counter electrode 210 may be at a level higher than the potential of working electrode 202 (and integrating capacitor 408), or vice versa. For example, during a positive phase of a square wave from voltage source (e.g. a signal generator) $V_{LIQ}$ (e.g., the bright or dark period of the AC voltage source signal cycle), the potential of counter electrode 210 is at a level higher than the potential of working electrode 202. During a negative phase of the square wave from voltage source $V_{LIQ}$ (e.g., the dark or bright period of the AC voltage source signal cycle), the potential of counter electrode 210 is at a level lower than the potential of working electrode 202. Thus, in some embodiments, integrating capacitor 408 may be further charged during the bright period from the pre-charged voltage level of voltage source $V_{PRE}$ 405 to a higher level, and discharged during the dark period to a lower level, due to the potential difference between counter electrode 210 and working electrode 202. In other embodiments, the charging and discharging may occur in dark periods and bright periods, respectively.

Integrating capacitor 408 may be charged or discharged for a fixed period of time, depending on the sampling rate of an analog-to-digital converter (ADC) 410, which may be higher than 1 kHz, 5 kHz, 10 kHz, 100 kHz, or more. For example, with a sampling rate of 1 kHz, integrating capacitor 408 may be charged/discharged for a period of about 1 ms, and then the voltage level may be sampled and converted by ADC 410 at the end of the integration period. A particular voltage level would correspond to a particular tag species in the nanopore, and thus correspond to the nucleotide at a current position on the template.

After being sampled by ADC 410, integrating capacitor 408 may be pre-charged again by using reset signal 403 to close switch 401, such that integrating capacitor 408 is connected to voltage source $V_{PRE}$ 405 again. The steps of pre-charging integrating capacitor 408, waiting for a fixed period of time for integrating capacitor 408 to charge or discharge, and sampling and converting the voltage level of integrating capacitor by ADC 410 can be repeated in cycles throughout the sequencing process.

A digital processor 430 can process the ADC output data, e.g., for normalization, data buffering, data filtering, data compression, data reduction, event extraction, or assembling ADC output data from the array of nanopore cells into various data frames. In some embodiments, digital processor 430 can perform further downstream processing, such as base determination. Digital processor 430 can be implemented as hardware (e.g., in a GPU, FPGA, ASIC, etc.) or as a combination of hardware and software.

Accordingly, the voltage signal applied across the nanopore can be used to detect particular states of the nanopore. One of the possible states of the nanopore is an open-channel state when a tag-attached polyphosphate is absent from the barrel of the nanopore, also referred to herein as the unthreaded state of the nanopore. Another four possible states of the nanopore each correspond to a state when one of the four different types of tag-attached polyphosphate nucleotides (A, T, G, or C) is held in the barrel of the nanopore. Yet another possible state of the nanopore is when the lipid bilayer is ruptured.

When the voltage level on integrating capacitor 408 is measured after a fixed period of time, the different states of a nanopore may result in measurements of different voltage levels. This is because the rate of the voltage decay (decrease by discharging or increase by charging) on integrating capacitor 408 (i.e., the steepness of the slope of a voltage on integrating capacitor 408 versus time plot) depends on the nanopore resistance (e.g., the resistance of resistor $R_{PORE}$ 428). More particularly, as the resistance associated with the nanopore in different states is different due to the molecules' (tags') distinct chemical structures, different corresponding rates of voltage decay may be observed and may be used to identify the different states of the nanopore. The voltage decay curve may be an exponential curve with an RC time constant $\tau=RC$, where R is the resistance associated with the nanopore (i.e., $R_{PORE}$ 428) and C is the capacitance associated with the membrane (i.e., capacitor 426 ($C_{Bilayer}$)) in parallel with R. A time constant of the nanopore cell can be, for example, about 200-500 ms. The decay curve may not fit exactly to an exponential curve due to the detailed implementation of the bilayer, but the decay curve may be similar to an exponential curve and is monotonic, thus allowing detection of tags.

In some embodiments, the resistance associated with the nanopore in an open-channel state may be in the range of 100 MOhm to 20 GOhm. In some embodiments, the resistance associated with the nanopore in a state where a tag is inside the barrel of the nanopore may be within the range of 200 MOhm to 40 GOhm. In other embodiments, integrating capacitor 408 may be omitted, as the voltage leading to ADC 410 will still vary due to the voltage decay in electrical model 422.

The rate of the decay of the voltage on integrating capacitor 408 may be determined in different ways. As explained above, the rate of the voltage decay may be determined by measuring a voltage decay during a fixed time interval. For example, the voltage on integrating capacitor 408 may be first measured by ADC 410 at time t1, and then the voltage is measured again by ADC 410 at time t2. The voltage difference is greater when the slope of the voltage on integrating capacitor 408 versus time curve is steeper, and the voltage difference is smaller when the slope of the voltage curve is less steep. Thus, the voltage difference may be used as a metric for determining the rate of the decay of the voltage on integrating capacitor 408, and thus the state of the nanopore cell.

In other embodiments, the rate of the voltage decay can be determined by measuring a time duration that is required for a selected amount of voltage decay. For example, the time required for the voltage to drop or increase from a first voltage level V1 to a second voltage level V2 may be measured. The time required is less when the slope of the voltage vs. time curve is steeper, and the time required is greater when the slope of the voltage vs. time curve is less steep. Thus, the measured time required may be used as a metric for determining the rate of the decay of the voltage on integrating capacitor $n_{cap}$ 408, and thus the state of the nanopore cell. One skilled in the art will appreciate the various circuits that can be used to measure the resistance of the nanopore, e.g., including current measurement techniques.

In some embodiments, electric circuit 400 may not include a pass device (e.g., pass device 406) and an extra capacitor (e.g., integrating capacitor 408 ($n_{cap}$)) that are fabricated on-chip, thereby facilitating the reduction in size of the nanopore-based sequencing chip. Due to the thin nature of the membrane (lipid bilayer), the capacitance associated with the membrane (e.g., capacitor 426 ($C_{Bilayer}$)) alone can suffice to create the required RC time constant without the need for additional on-chip capacitance. Therefore, capacitor 426 may be used as the integrating capacitor, and may be pre-charged by the voltage signal $V_{PRE}$ and subsequently be discharged or charged by the voltage signal $V_{LIQ}$. The elimination of the extra capacitor and the pass device that are otherwise fabricated on-chip in the electric circuit can significantly reduce the footprint of a single nanopore cell in the nanopore sequencing chip, thereby facilitating the scaling of the nanopore sequencing chip to include more and more cells (e.g., having millions of cells in a nanopore sequencing chip).

D. Data Sampling in Nanopore Cell

To perform sequencing of a nucleic acid, the voltage level of integrating capacitor (e.g., integrating capacitor 408 ($n_{cap}$) or capacitor 426 ($C_{Bilayer}$)) can be sampled and converted by the ADC (e.g., ADC 410) while a tagged nucleotide is being added to the nucleic acid. The tag of the nucleotide can be pushed into the barrel of the nanopore by the electric field across the nanopore that is applied through the counter electrode and the working electrode, for example, when the applied voltage is such that $V_{LIQ}$ is lower than $V_{PRE}$.

1. Threading

A threading event is when a tagged nucleotide is attached to the template (e.g., nucleic acid fragment), and the tag goes in and out of the barrel of the nanopore. This can happen multiple times during a threading event. When the tag is in the barrel of the nanopore, the resistance of the nanopore may be higher, and a lower current may flow through the nanopore.

During sequencing, a tag may not be in the nanopore in some AC cycles (referred to as an open-channel state), where the current is the highest because of the lower resistance of the nanopore. When a tag is attracted into the barrel of the nanopore, the nanopore is in a bright mode. When the tag is pushed out of the barrel of the nanopore, the nanopore is in a dark mode.

2. Bright and Dark Period

During an AC cycle, the voltage on integrating capacitor may be sampled multiple times by the ADC. For example, in one embodiment, an AC voltage signal is applied across the system at, e.g., about 100 Hz, and an acquisition rate of the ADC can be about 2000 Hz per cell. Thus, there can be about 20 data points (voltage measurements) captured per AC cycle (cycle of an AC waveform). Data points corresponding to one cycle of the AC waveform may be referred to as a set. In a set of data points for an AC cycle, there may be a subset captured when, for example, $V_{LIQ}$ is lower than $V_{PRE}$, which may correspond to a bright mode (period) where the tag is forced into the barrel of the nanopore. Another subset may correspond to a dark mode (period) where the tag is pushed out of the barrel of the nanopore by the applied electric field when, for example, $V_{LIQ}$ is higher than $V_{PRE}$.

3. Measured Voltages

For each data point, when the switch 401 is opened, the voltage at the integrating capacitor (e.g., integrating capacitor 408 ($n_{cap}$) or capacitor 426 ($_{Bilayer}$)) will change in a decaying manner as a result of the charging/discharging by $V_{LIQ}$, e.g., as an increase from $V_{PRE}$ to $V_{LIQ}$ when $V_{LIQ}$ is higher than $V_{PRE}$ or a decrease from $V_{PRE}$ to $V_{LIQ}$ when $V_{LIQ}$ is lower than $V_{PRE}$. The final voltage values may deviate from $V_{LIQ}$ as the working electrode charges. The rate of change of the voltage level on the integrating capacitor may be governed by the value of the resistance of the bilayer, which may include the nanopore, which may in turn include a molecule (e.g., a tag of a tagged nucleotides) in the nanopore. The voltage level can be measured at a predetermined time after switch 401 opens.

Switch 401 may operate at the rate of data acquisition. Switch 401 may be closed for a relatively short time period between two acquisitions of data, typically right after a measurement by the ADC. The switch allows multiple data points to be collected during each sub-period (bright or dark) of each AC cycle of $V_{LIQ}$. If switch 401 remains open, the voltage level on the integrating capacitor, and thus the output value of the ADC, would fully decay and stay there. Instead, when switch 401 is closed, the integrating capacitor is precharged again (to $V_{PRE}$) and becomes ready for another measurement. Thus, switch 401 allows multiple data points to be collected for each sub-period (bright or dark) of each AC cycle. Such multiple measurements can allow higher resolution with a fixed ADC (e.g. 8-bit to 14-bit due to the greater number of measurements, which may be averaged). The multiple measurements can also provide kinetic information about the molecule threaded into the nanopore. The timing information may allow the determination of how long a threading takes place. This can also be used in helping to determine whether multiple nucleotides that are added to the nucleic acid strand are being sequenced.

Figure 5:
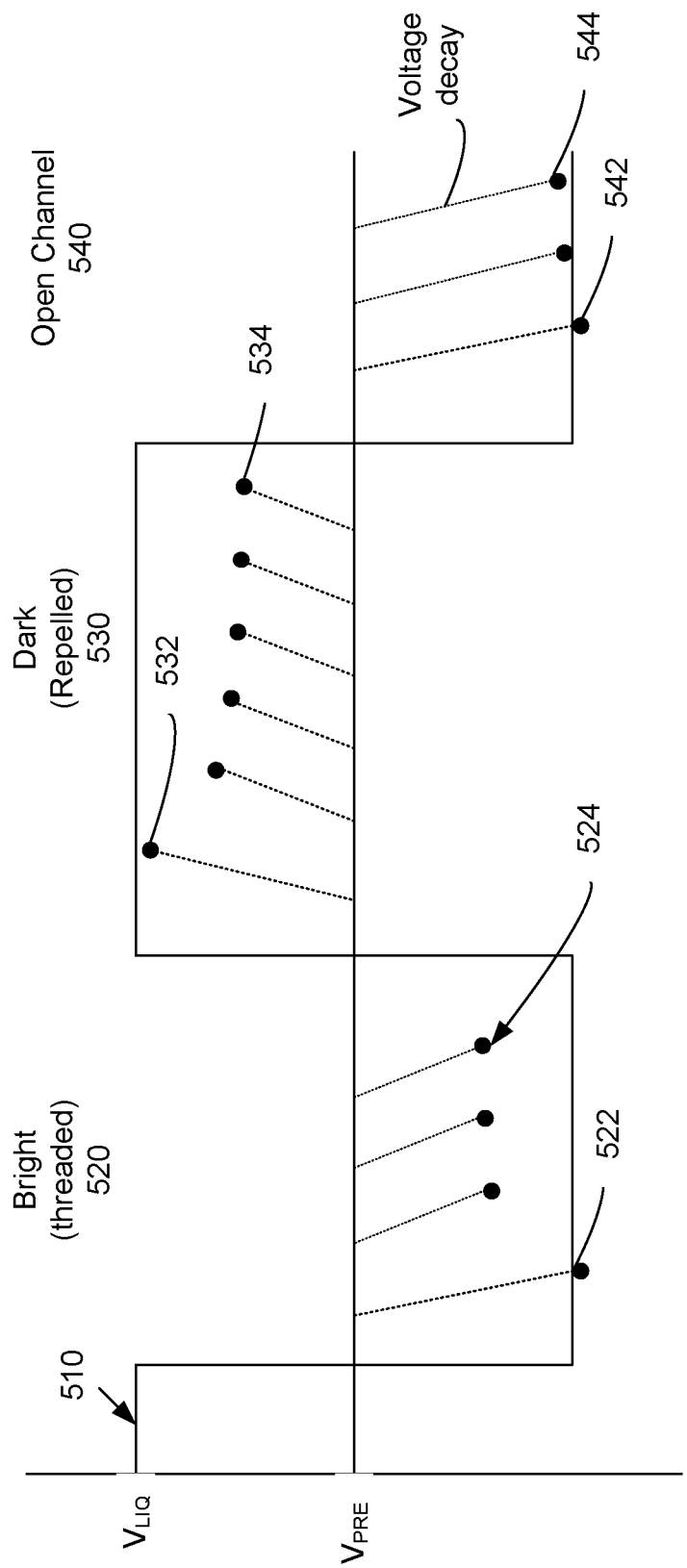
FIG. 5 shows example data points captured from a nanopore cell during bright periods and dark periods of AC cycles.

FIG. 5 shows example data points captured from a nanopore cell during bright periods and dark periods of AC cycles. In FIG. 5, the change in the data points is exaggerated for illustration purpose. The voltage ($V_{PRE}$) applied to the working electrode or the integrating capacitor is at a constant level, such as, for example, 900 mV. A voltage signal 510 ($V_{LIQ}$) applied to the counter electrode of the nanopore cells is an AC signal shown as a rectangular wave, where the duty cycle may be any suitable value, such as less than or equal to 50%, for example, about 40%.

During a bright period 520, voltage signal 510 ($V_{LIQ}$) applied to the counter electrode is lower than the voltage $V_{PRE}$ applied to the working electrode, such that a tag may be forced into the barrel of the nanopore by the electric field caused by the different voltage levels applied at the working electrode and the counter electrode (e.g., due to the charge on the tag and/or flow of the ions). When switch 401 is opened, the voltage at a node before the ADC (e.g., at an integrating capacitor) will decrease. After a voltage data point is captured (e.g., after a specified time period), switch 401 may be closed and the voltage at the measurement node will increase back to $V_{PRE}$ again. The process can repeat to measure multiple voltage data points. In this way, multiple data points may be captured during the bright period.

As shown in FIG. 5, a first data point 522 (also referred to as first point delta (FPD)) in the bright period after a change in the sign of the $V_{LIQ}$) signal may be lower than subsequent data points 524. This may be because there is no tag in the nanopore (open channel), and thus it has a low resistance and a high discharge rate. In some instances, first data point 522 may exceed the $V_{LIQ}$ level as shown in FIG. 5. This may be caused by the capacitance of the bilayer coupling the signal to the on-chip capacitor. Data points 524 may be captured after a threading event has occurred, i.e., a tag is forced into the barrel of the nanopore, where the resistance of the nanopore and thus the rate of discharging of the integrating capacitor depends on the particular type of tag that is forced into the barrel of the nanopore. Data points 524 may decrease slightly for each measurement due to charge built up at $C_{Double\ Layer}$ 424, as mentioned below.

During a dark period 530, voltage signal 510 ($V_{LIQ}$) applied to the counter electrode is higher than the voltage ($V_{PRE}$) applied to the working electrode, such that any tag would be pushed out of the barrel of the nanopore. When switch 401 is opened, the voltage at the measurement node increases because the voltage level of voltage signal 510 ($V_{LIQ}$) is higher than $V_{PRE}$. After a voltage data point is captured (e.g., after a specified time period), switch 401 may be closed and the voltage at the measurement node will decrease back to $V_{PRE}$ again. The process can repeat to measure multiple voltage data points. Thus, multiple data points may be captured during the dark period, including a first point delta 532 and subsequent data points 534. As described above, during the dark period, any nucleotide tag is pushed out of the nanopore, and thus minimal information about any nucleotide tag is obtained, besides for use in normalization.

FIG. 5 also shows that during bright period 540, even though voltage signal 510 ($V_{LIQ}$) applied to the counter electrode is lower than the voltage ($V_{PRE}$) applied to the working electrode, no threading event occurs (open-channel). Thus, the resistance of the nanopore is low, and the rate of discharging of the integrating capacitor is high. As a result, the captured data points, including a first data point 542 and subsequent data points 544, show low voltage levels.

The voltage measured during a bright or dark period might be expected to be about the same for each measurement of a constant resistance of the nanopore (e.g., made during a bright mode of a given AC cycle while one tag is in the nanopore), but this may not be the case when charge builds up at double layer capacitor 424 ($C_{Double\ Layer}$). This charge build-up can cause the time constant of the nanopore cell to become longer. As a result, the voltage level may be shifted, thereby causing the measured value to decrease for each data point in a cycle. Thus, within a cycle, the data points may change somewhat from data point to another data point, as shown in FIG. 5.

4. Determining Bases

For each usable nanopore cell of the nanopore sensor chip, a production mode can be run to sequence nucleic acids. The ADC output data captured during the sequencing can be normalized to provide greater accuracy. Normalization can account for offset effects, such as cycle shape and baseline shift. After normalization, embodiments can determine clusters of voltages for the threaded channels, where each cluster corresponds to a different tag species, and thus a different nucleotide. The clusters can be used to determine probabilities of a given voltage corresponding to a given nucleotide. As another example, the clusters can be used to determine cutoff voltages for discriminating between different nucleotides (bases).

Further details regarding the sequencing operation can be found in, for example, U.S. Patent Publication No. 2016/0178577 entitled "Nanopore-Based Sequencing With Varying Voltage Stimulus," U.S. Patent Publication No. 2016/0178554 entitled "Nanopore-Based Sequencing With Varying Voltage Stimulus," U.S. patent application Ser. No.

15/085,700 entitled "Non-Destructive Bilayer Monitoring Using Measurement Of Bilayer Response To Electrical Stimulus," and U.S. patent application Ser. No. 15/085,713 entitled "Electrical Enhancement Of Bilayer Formation," the disclosures of which are incorporated by reference in their entirety for all purposes.

III. Overview of Calibration and Normalization Pipeline

Figure 6:
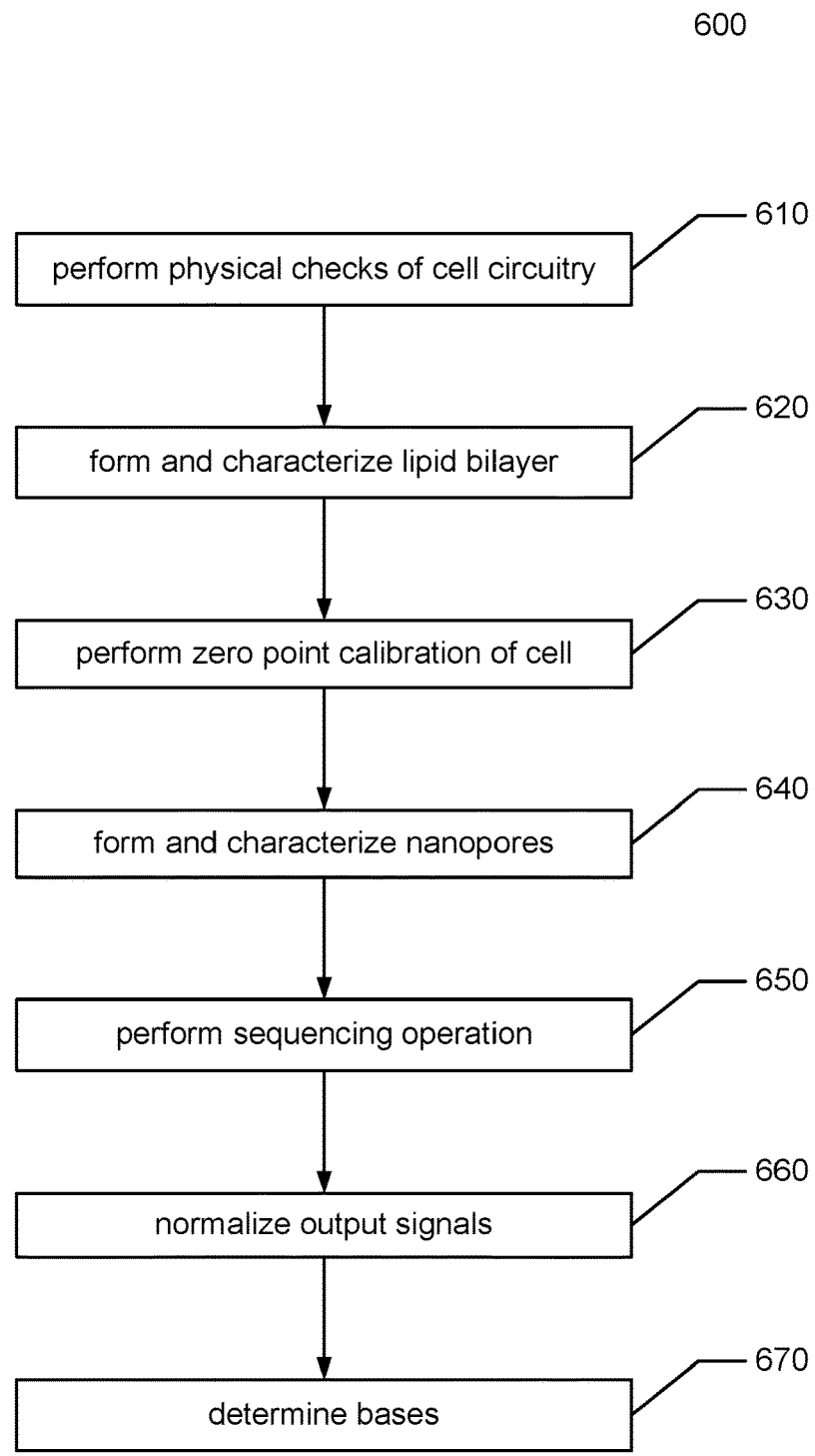
FIG. 6 shows a flow chart illustrating an example method of formation and calibration of nanopore sequencing cells according to certain embodiments.

FIG. 6 is a flow chart illustrating an example method of formation and calibration of nanopore sequencing cells according to certain embodiments. As part of calibration, various checks can be made during creation of the sequencing cell. Once a cell is created, further calibration steps can be performed, e.g., to identify sequencing cells that are performing as desired (e.g., one nanopore in the cell). Once the calibration steps are completed, normalization and sequencing can be performed.

In step 610, physical checks of a cell's circuitry are performed. Some "dry checks" can be performed before any buffer or lipid solution is applied, and some "wet checks" can be performed after buffer and or lipid solution is applied. For example, each cell of the sequencing chip may be checked for an open-circuit or short-circuit state. Further description of the physical checks according to certain embodiments can be found below in reference to Section IV(A).

In step 620, a lipid layer is formed over each cell. According to certain embodiments, the thickness of the lipid layer is monitored during the formation process, and various feedback processes may operate to ensure that the eventual state of the lipid layer is that of a lipid bilayer. For example, if after a first iteration of applying a lipid solution to a cell it is determined that the lipid layer is too thick and not a bilayer, a thinning procedure may be initiated. Further description of the physical checks associated with the lipid bilayer according to certain embodiments can be found below in reference to Section IV(A).

In step 630, a zero point voltage calibration is performed for each cell of the sequencing chip. Due to variations in the electronic properties of each cell, each cell can have a different DC offset with zero volts applied to the cell. The DC offset is referred to herein as a "zero point" voltage and, alternatively, as VMzero. For example, there can be manufacturing imperfections or variation between the analog circuitry of different cells in the chip. Thus, the ADC for one cell can have a different voltage bias than the ADC for another cell. Embodiments can perform calibration to account for such variation. Further description of the zero point voltage calibration according to certain embodiments can be found below in reference to Section IV(B).

In step 640, nanopores are added to each cell, and the cells are characterized to determine how many nanopores per cell have been added. At this step, if too many (more than one) or too few (zero) nanopores have been added to a cell, a feedback process may be initiated to either add or remove nanopore(s) from the cell. According to certain embodiments, cells that are found to have more or less than one nanopore can be deactivated and not used during the sequencing process. Further description of the nanopore characterization according to certain embodiments can be found below in reference to Section IV(C) and IV(E). According to certain embodiments, the nanopore characterization method may be performed by a digital processor as described above in reference to FIG. 4 and as described below in reference to FIG. 15 and FIG. 19.

In step 650, a sequencing operation is performed, thereby generating output signals from the cells, e.g., as described above in reference to FIGS. 3-5. For example, a tail of a tag may be positioned in the barrel of the nanopore, thereby generating a unique output signal due to the tag's distinct chemical structure and/or size. According to certain embodiments, the output signals may be measured via a current passing through the nanopore, thereby providing an identification of the tag species and thus the nucleotide at a current position in a nucleic acid. In some embodiments, the current or a voltage may be measured by way of an integrating capacitor, e.g., as described above in reference to FIGS. 4-5.

In step 660, the output signals (e.g., voltage and/or current signals) are normalized. Part of this normalization process can involve measuring and or inferring (through the use of an analog circuit model of the cell) a bright mode open channel voltage and using that bright mode open channel voltage as a normalization factor for the output signals. Further description of the normalization process according to certain embodiments can be found below in reference to Section IV(D) and Section V(A)-(G). According to certain embodiments, the normalization method may be performed by a digital processor as described above in reference to FIG. 4 and as described below in reference to FIG. 15 and FIG. 19.

While sequencing, calibration, and normalization are shown here as separate steps, these steps may be performed together as part of the sequencing operation, i.e., each point or group of points that are acquired during sequencing may be subject to a calibration and normalization step without departing from the scope of the present disclosure.

In step 670, one or more processors may determine bases using the normalized output signals. As described in Section VI below, embodiments can determine clusters of voltages for the threaded channels, and use the clusters to determine cutoff voltages for discriminating between different bases using the normalized output signals.

According to certain embodiments, the order of the calibration and normalization checks may be different than that shown in the flow chart of FIG. 6. For example, according to certain embodiments, the calibration and normalization step may be performed once, e.g., after an initial manufacturing processing step is complete (e.g. before formation of the lipid bilayer, after formation of the lipid bilayer, before formation of the nanopore, after formation of the nanopore, etc.). According to certain embodiments, calibration may be done many times over the life of a chip (e.g., at scheduled intervals and/or before every sequencing operation). According to certain embodiments calibration and normalization may be done in an "online" manner, i.e. for each raw data point acquired or every time a group of raw data points is acquired.

IV. Calibration

Calibration of a sequencing chip can be performed before sequencing starts. The calibration can be performed to ensure that no critical errors exist, where such critical errors might prevent sequencing to be performed in one or more cells. Calibration can also be used to obtain calibration values (e.g., to determine a zero-point voltage) that are used in measuring values (e.g., voltages or currents) or used in analyzing measured values to obtain corrected or normalized voltage values, which can ultimately be used to determine sequence of a nucleic acid.

A. Physical Checks

A dry check can occur before any buffer (e.g., an electrolyte solution) is flowed into the sequencing chip and before a membrane (e.g., a lipid bilayer) is formed over a well. In a dry check, the electrical components of the sequence chip (e.g., for each sequencing cell) are checked to confirm they are functioning properly, e.g., a signal with an expected value (e.g., within a specific range) is received from each well. At this point, there should be no connection between the electrodes (e.g., electrodes 202 and 210), since there is no electrolyte solution in the well or sample chamber. If there is a connection (e.g., a short) then the measured voltage would be outside of an expected range (e.g., a voltage measurement being the same as the reference voltage), thereby indicating there is something wrong.

In a wet check, buffer is flowed over the surface of the chip. This check can make sure that there is a connection (e.g., a short) between the electrodes. If there is no connection then, that indicates a problem.

In a lipid (cover) check, a solution can be flowed over the chip. The solution can be an organic solvent with the lipid dissolved in it. At the end of that process, each well should have a plug of the solvent and lipid. There should be no (or minimal) electrical connection between the electrodes at this point as the lipid layer would be too thick.

In a thinning procedure, the ADC value can be measured for each cell to determine cells where the lipid layer is too thick, and the bilayer can be thinned. U.S. patent application Ser. No. 15/085,713 describes an electrical lipid-thinning stimulus to thin the lipid layer.

A cell can start with a relatively thick lipid layer, which is thinned to form a lipid bilayer. After thinning, there can be a two-molecule-thick lipid bilayer that acts as a membrane to cover the well. In practice, any water-permeable membrane may be used. On the edges of the lipid bilayer is an annulus, an anchoring ring of solvent. The annulus can act as a reservoir of lipids for the bilayer.

The thickness of the lipid layer can be measured using the first point delta (FPD), which corresponds to the difference between the first measured voltage points in the bright mode and dark mode respectively, e.g., FPD is the difference between the high first points shown in FIG. 5. The first point delta is proportional to the capacitance of the bilayer, and the bilayer thicknesses is proportional to capacitance. When the lipid layer is thick (e.g., microns), then the capacitance is small. By the time the thickness shrinks down to about 4 nm, the capacitance is something measurable, e.g., on the order of 100 femtofarads. A bilayer has a deterministic thickness, based on the molecules used, with some small differences based on how the molecules of the bilayer are arranged and how much solvent remains. According to certain embodiments, the thickness of the lipid bilayer may be from 4.2 to 4.3 nm.

The capacitance of the bilayer (or other membrane) is proportional to the lateral area, which depends on how much annulus exists. Thus, the FPD can provide whether the bilayer exists and how close to the edge the bilayer has formed.

In some embodiments, a feedback mechanism in the system can be used to further thin the bilayer. To thin the lipid layer, a lateral pressure can be applied (e.g., flowing buffer at high velocity across top of the lipid layer). As another example, one can turn on the AC signal to apply an AC bias, which can effectively shake the layer back and forth until it achieves the energetically stable state of the bi-layer. Such a procedure can remove any local minimum in the formation process of the lipid bilayer.

The feedback can act by measuring the FPD over time and adjusting the feedback. The cells with a sufficiently small FPD (e.g., below a threshold) can have actions performed to thin that particular cell. Such a process can continue until at least a specified percentage of cells (e.g., 70%) have a usable bilayer.

B. Voltage Calibration

To calibrate the system for different voltages, a zero-point voltage of each cell (also referred to herein as VMzero) can be determined. For electronic reasons, each cell can have a different DC offset. For example, there can be manufacturing imperfections or variations between the analog circuitry of different cells in the chip. Also, a bias can be built into the system for electrochemical reasons. Due to such manufacturing variability, one electrode can be slightly different than another. This can introduce an offset from cell to cell. In addition, the surface chemistry of the electrodes may make them act as batteries, and thus each cell may have a slightly different potential, which can contribute to the VMzero for each cell. According to certain embodiments, a net effect is that the measured ADC signal is pushed up or down, depending on the value of VMzero. Embodiments can perform a calibration to account for such variation between cells.

Figure 7:
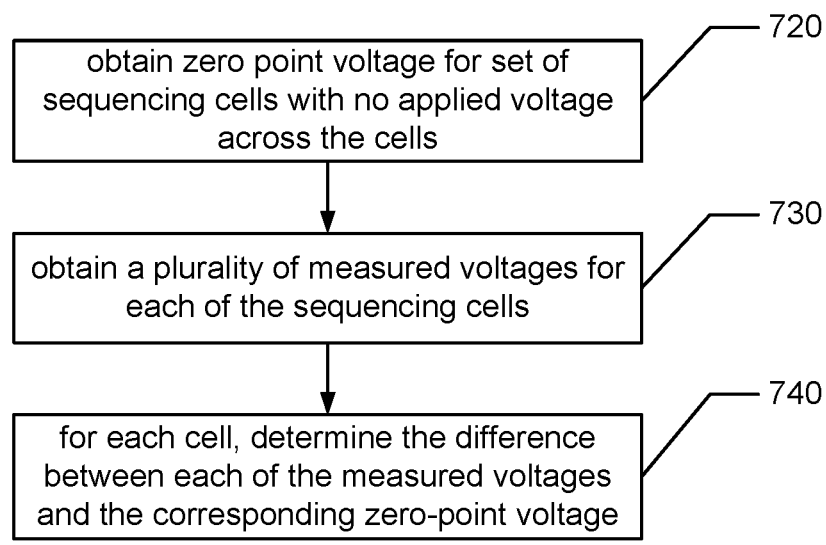
FIG. 7 shows a flow chart illustrating an example method of calibration of nanopore sequencing cells for a sequencing chip according to certain embodiments.

FIG. 7 is a flow chart illustrating an example method 700 of calibration of nanopore sequencing cells for a sequencing chip according to certain embodiments. Method 700 can be performed at various times, e.g., before a membrane has been formed, after a membrane has been formed (but before a pore is inserted), and/or after a pores have been inserted into the cells. This calibration can be performed at multiple times in a calibration process, with different values for VMzero being obtained and used for a given stage.

In step 720, a zero point voltage (also referred to herein as VMzero) is obtained for each cell of the sequencing chip. In some embodiments, VMZero is measured by the ADC with zero voltage applied to the cell (e.g., no pathway for current flow). Such a state of zero applied voltage can be achieved in various ways, e.g., by disconnecting the working electrode and/or the counter electrode or by having both electrodes be at a same voltage. In this manner, each ADC may receive a different floating voltage. Furthermore, the conversion from the analog value to the digital can vary from ADC to ADC. According to certain embodiments, the measured set of VMzeros, one for each cell, can be stored in memory. These stored values can be used to calibrate (i.e., remove the offset from) each cell, thereby ensuring that the ADC measurements of both bright and/or dark period voltages are comparable from cell to cell. As described above, the zero point voltage for each cell can be measured by an ADC, e.g., ADC 410 shown in FIG. 4.

The sequencing chip may include thousands or even millions of cells, and thus thousands or even millions of zero point voltages can be measured. According to certain embodiments, the zero point voltages may be measured and stored in memory before the nanopores are inserted into the lipid bilayers of each cell. In some embodiments, the memory may be integrated onto the sequencing chip or may be an external memory store that is operatively connected to the sequencing chip, e.g., such as any form of computer memory, as described below in reference to FIG. 20. Alternatively or additionally, the zero point voltages may be measured after the nanopores are inserted into the lipid bilayers of each cell. As a further example, the zero point voltages may be measured once for each chip as part of a characterization or calibration step or may be measured multiple times over the lifetime of the chip. For example, VMzero may change over time as the capacitance of the double layer capacitor changes, and thus may be measured before and/or after a sequencing run to ensure that the system is calibrated properly. More details about how the double layer capacitance contributes to VMzero is described in more detail below in Section V(D)(2).

In step 730, after the nanopores have been inserted into the lipid bilayers, a sequencing operation may be performed and a plurality of measured voltages may be obtained (e.g., by the ADCs of the sequencing chip). The sequencing may be performed during the application of an alternating signal across each cell of the chip. The process of obtaining voltage data in this manner is described above in reference to FIGS. 3-5.

In step 740, the obtained voltage values are corrected using the stored VMzero values. For example, according to certain embodiments, a difference between a cell's measured values and its VMzero value can be computed, e.g., by a digital processor 430 in FIG. 4. More specifically, a set of corrected or calibrated voltage values can be obtained for each cell by subtracting that cell's VMzero from the measured voltage values.

Accordingly, a zero point voltage value (e.g., as VMzero) can be determined for each cell and used to optimize the dynamic range of the ADC. For example, an ADC can provide a specified data range, e.g., an 8-bit unsigned range (0 to 255). The difference between the digital values are controlled by the manufacturing of the ADC, but the specific analog range can be varied (e.g., as controlled by an ADC reference voltage) to correspond to an expected range of the analog voltage for the sequencing cells, taking into account the cell-specific VMzero. The zero value for the ADC need not correspond to zero volts, as the relative voltages is what is used.

In one embodiment, there are two reference voltages that set the bottom and the top of the ADC voltage range. The two voltages can be of different sign. The reference voltages can be set externally. The reference voltages can be changed as different biochemistry is used. The actual signal should be within the reference range, and ideally take up most of that reference range. According to certain embodiments, knowledge of the measured VMzero for each cell can may be used to set the reference voltages for each cell independently. This can ensure that the full dynamic range of the ADC is being used, thereby minimizing quantization noise.

C. Insertion of Nanopore

Nanopores can be inserted into the lipid bilayer a number of different ways. For example, if relying on force of pressure in the chip to randomly diffuse the pores into the membranes, then the proportion would be governed by binomial distribution. In such a situation, many cells would have zero nanopores, some would have one, some would have two, and the majority would not have just one. However, according to certain embodiments, just one nanopore per cell is best for sequencing. If there are more than one nanopore per cell, e.g., two nanopores per cell, then the signal from the pore will be some combination of the two signals from the two pores, which can cause the levels to have error, as such a system has a different equivalent circuit than a single pore cell. Furthermore, the combined signal would results from tags entering the nanopore at different times, making it difficult to know which base to call at a given time.

According to certain embodiments, electroporation can be used to insert the nanopores into the bilayer. Electroporation applies a square wave across the bilayer to stress it. Too high a voltage would pop the lipid layer. But, a suitable voltage can provide a tear where the nanopore can be inserted more easily.

As mentioned above, it is beneficial for each cell to have exactly one nanopore. To accomplish this, according to certain embodiments a diagnostic measurement can be taken for each cell before, during, and after the electroporation signal is applied, e.g., a voltage value akin to an open channel measurement described above in reference to FIGS. 4-5 can be measured. The measured value can then be then analyzed to determine whether the measured value corresponds to a value that would be expected for a cell having only one nanopore. A single nanopore may be detected by tracking a voltage changes during the electroporation process, and if the voltage changes significantly then it is assumed that proration has successfully completed.

When a nanopore is observed to have been added to a cell, the electroporation process can be stopped for that well. This can be done independently for each well. As described in further detail below, the above process can be used in combination with a diagnostic technique that employs a voltage histogram/distribution of the open channel voltages for all the cells across the sequencing chip to identify an open-channel voltage, or range of open channel voltages, that indicate a single nanopore cell. For those cells that do not have any pores after the first electroporation step, the electroporation may be repeated.

D. Open Channel Calibration

After electroporation, the output voltage of a cell with no tag in place can be measured to determine the initial voltage of the cell. As described above in reference to FIGS. 4-5, this measured ADC value is referred to as an open channel voltage. The value of the open channel voltage can be used in normalization, as described later. In addition, the value of the open channel can be used to identify cells with a single nanopore, as described in the next section.

According to certain embodiments, as part of the open channel calibration process, the cycle decay shape can also be determined, as described above in reference to FIGS. 4-5. For example, in response to an alternating signal ($V_{LIQ}$) provided to the counter electrodes, an ADC may measure an output voltage on an integrating capacitor, e.g., integrating capacitor 408 of FIG. 4. As shown in FIG. 5, the voltage measured by the ADC does not exactly track the square wave drive signal, but rather can show a decay over the bright or dark periods within each cycle of the drive signal $V_{LIQ}$ as a result of the buildup of charge on $C_{Double\ Layer}$. According to certain embodiments, the resulting decay shape of each period within one AC cycle can be measured as part of the open channel calibration process. The initial value of the open channel can help determine the expected value for the channels corresponding to different molecules (e.g., four different bases). For instance, the cycle decay shape can be used to identify the spread in voltages for a given threaded cycle of one tag relative to the different in voltage expected for different tags.

In some embodiments, the open channel calibration can be performed for each cell of the sequencing chip immediately after the poration process is complete. The open channel calibration process can leverage the presence of open channel data during a sequencing operation, and thus can be performed as part of a preprocessing step during the data normalization process described in detail below.

E. Identification of Wells with Single Nanopore

As mentioned above, it is desired that each cell of the sequencing chip have only one nanopore. According to certain embodiments, the cells with one nanopore can be identified by a statistical analysis of the magnitudes of the open channel voltages (e.g., the measured ADC value during bright or dark mode, without a tag present in the nanopore). A histogram (or distribution) of the measured voltages can be computed by binning the measured voltages and counting the number of cells having voltages that fall within a particular voltage bin. The histogram can be analyzed to determine the largest amplitude peak, i.e. the most common voltages amongst the cells of the chip can be determined. The largest amplitude peak can be constrained to be within a certain expected range, which may be done by excluding a final bin of the histogram, which includes all measured voltages higher than a specified value.

According to certain embodiments, the most common voltages should correspond to the single nanopore cells, particularly when the electroporation process was monitored and subject to a feedback mechanism. Generally, the parameters of the poration process may be previously tuned such that for most cells, only a single pore will form, with a relatively small population forming more than one pore or no pore at all. In another embodiment, the second largest amplitude peak can be used as the peak corresponding to cells having only one nanopore, while the largest amplitude peak may correspond to cells with bare bilayers, i.e., zero nanopores.

Figure 8:
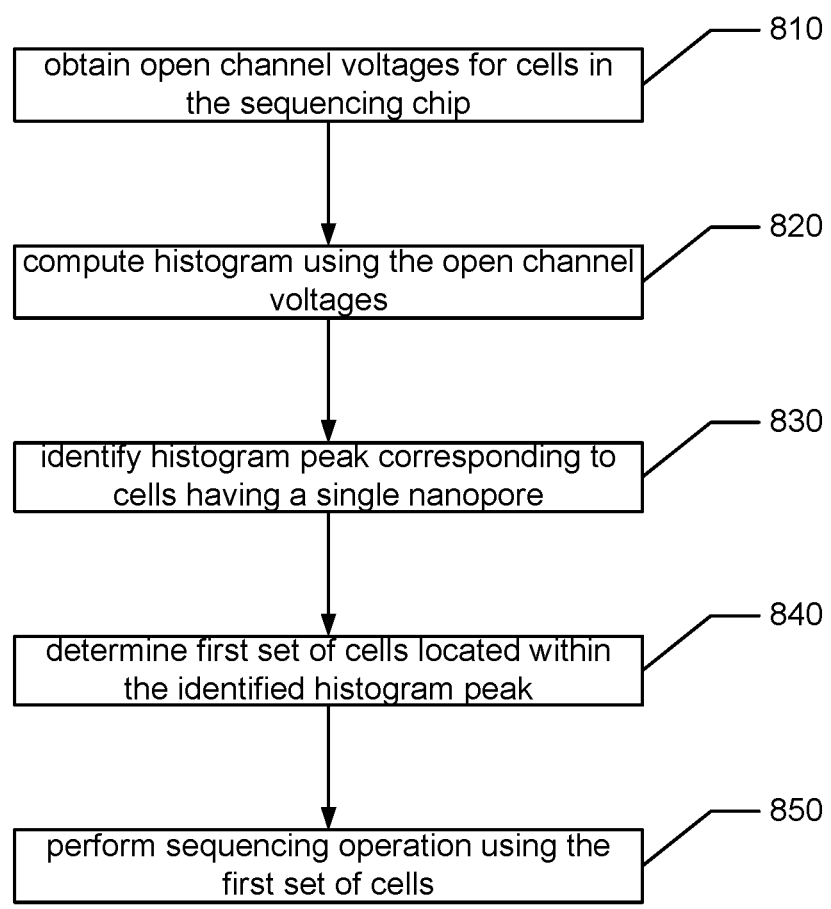
FIG. 8 shows a flow chart illustrating an example method of characterizing the number of nanopores in the cells of a sequencing chip according to certain embodiments.

FIG. 8 is a flow chart illustrating an example method 800 of characterizing the number of nanopores in the cells of a sequencing chip according to certain embodiments. Method 800 may be performed after a pore insertion process (or at least after an initial stage of pore insertion). Method 800 may be performed by processor 224 of FIG. 2, digital processor 430, and/or any control logic coupled with the circuits of the sequencing cell, including forward connections for the control logic to provide control signals (e.g., to control further poration steps).

In step 810, open channel voltages are obtained for cells in the sequencing chip. For example, the open channel voltages can be obtained in a similar manner to the voltages described above in reference to FIG. 5 and elsewhere in this disclosure. The obtaining of the open channel voltages may be achieved by receiving the voltages from the sequencing chip at a logic system, e.g., an FPGA, ASIC, or programmable processor.

Figures 9A, 9B, 9C:
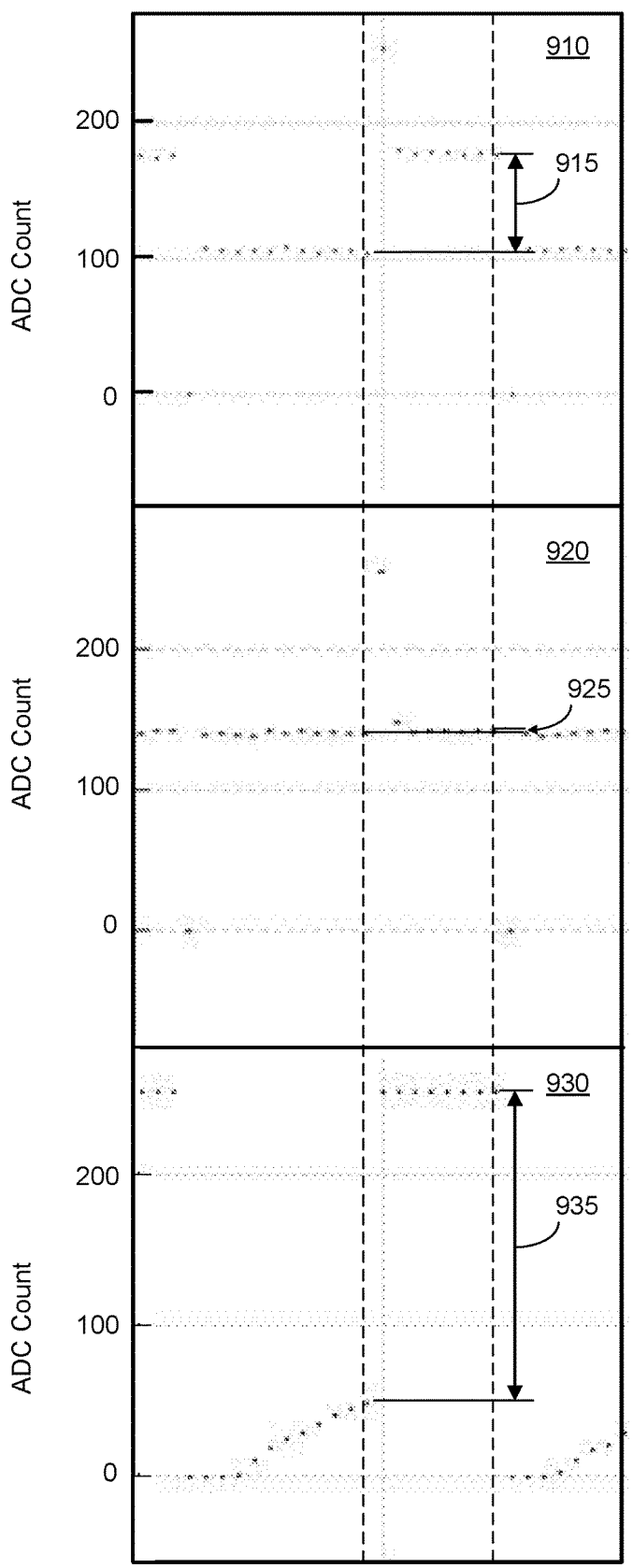
FIGS. 9A-9C show sample open channel voltage data for different states of the cell according to certain embodiments.

FIGS. 9A-9C show sample open channel voltage data for different states of the cell. FIG. 9A shows the open channel voltage data 910 (both bright and dark periods) for a cell having a single nanopore, referred to as a single nanopore cell. FIG. 9B shows the open channel voltage data 920 (both bright and dark periods) for a cell having zero nanopores, referred to as a zero cell bilayer. FIG. 9C shows the open channel voltage data 930 (both bright and dark periods) for a cell having a short circuit, referred to as a short circuited cell.

According to certain embodiments, the open channel voltages obtained in step 810 can be single point measurements or multi-point measurements. For example, a single bright channel data point (e.g., as shown in FIG. 9B) can be measured for each cell; and used to characterize the cell, i.e. whether the cell is single nanopore, zero nanopore, short, etc. A value for Vmzero may be subtracted from the data point for a given cell. For multipoint measurements, a collection of bright mode voltages can be averaged together, with Vmzero subtracted before or after the averaging. A multi-point method may involve computing difference data, e.g., point by point differences between bright and dark periods of one cycle, or point-by-point differences within a period of an AC cycle (e.g., difference between first and last points within a bright period or dark period).

FIGS. 9A-9C show a "last point delta" ("LPD") method that involves subtracting the last point of a bright period from a corresponding last point of a dark period, or vice versa. In FIG. 9A, the LPD 915 is about 80 ADC counts and represents the LPD of a single nanopore cell. In FIG. 9B, the LPD 925 is very nearly 0 ADC counts and represents the LPD of a zero nanopore cell (i.e. a cell having a bare bilayer). In FIG. 9C, the LPD 935 is about 190 ADC counts and represents the LPD of a short-circuited cell, which may correspond to a cell with no membrane or multiple pores. While the precise values of the ADC counts for each bilayer state may vary from cell to cell as described in further detail below, FIGS. 9A-9C show that in principle the LPD can be used to discriminate between different nanopore configurations on a cell's bilayer. Thus, according to certain embodiments, as part of step 810, the LPD of each cell is measured. As other examples, first point delta may be used or an average point delta (a difference between the average value for a bright and dark period). In other examples, the delta measurement may be made using points within the same period, in which case the measurement is referred to as a "decay delta" because the delta measures the amount of voltage decay within a cycle period, e.g., a dark decay delta may be computed by subtracting the $5^{th}$ and $10^{th}$ points of a measured during a dark period. In still yet other examples, the delta may be measured relative to a mean value that is measured outside of a normal bright or dark period, e.g., a "zero delta" may be used where the zero delta is measured between a bright period value and an offset value, e.g., a mean offset that is measured with zero volts applied across the cell In step 820, a histogram (also referred to herein as a voltage distribution) is computed using the voltage values obtained in step 810. The histogram may take as input, any type of measured voltages including both single point and/or multipoint measurements. For the example of the LPD described above, to compute the histogram, the full range of measured LPD values can be split into bins. For example, if the measured ADC counts range from 0 to 255, the data may be binned with one bin having a width of 1 ADC count, thereby having a histogram with 256 bins. Other bin widths (e.g., 2, 3, etc.) are possible without departing from the scope of the present disclosure. Once the bin width is chosen, the number of cells having that particular ADC value is counted and added to the histogram.

Figure 10:
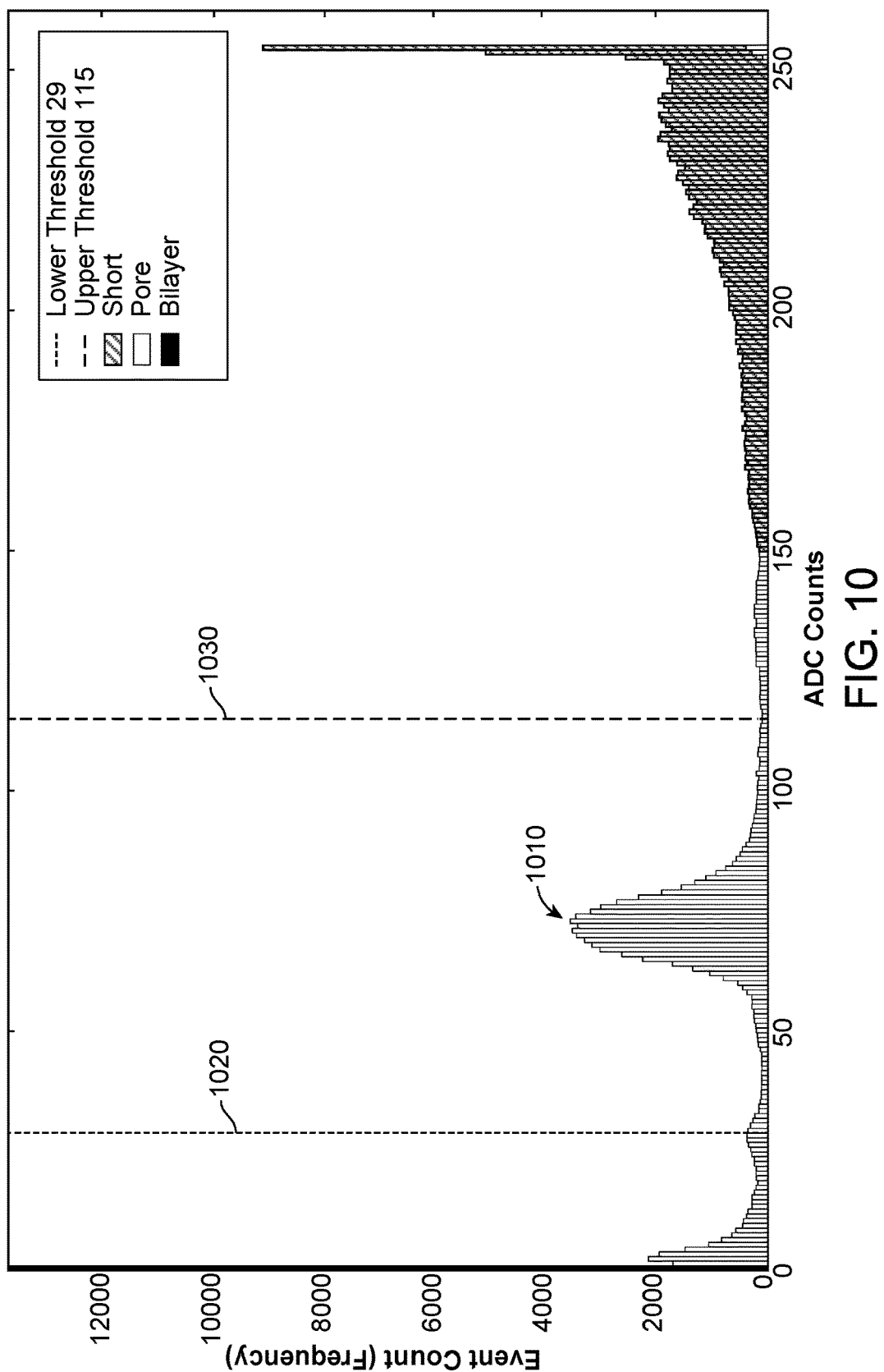
FIG. 10 shows sample histogram data according to certain embodiments.

FIG. 10 shows sample histogram data according to certain embodiments. A relatively large single nanopore peak 1010 is visible in the data. The leftmost portion of the histogram shows counts for cells having zero nanopores (low voltages) and also for cell having pseudo-pores, e.g., behavior that is similar to a pore. The rightmost portion of the histogram shows counts for cells that have more than one pore and also for cells that have short circuits (e.g., no membrane).

In step 830, a histogram peak corresponding to cells having a single nanopore (also referred to herein as single pore cells) is identified. According to certain embodiments, neither the peak value, nor the peak width needs to be known in advance of obtaining the measured voltage data in step 810. For example, a peak detection routine can detect boundaries and characteristics of the peaks, e.g., to identify the single nanopore peak. For instance, the center of the largest amplitude peak within a predetermined range of voltage values can be identified as the single nanopore peak. In some embodiments, the bins at or near the very end of the voltage range can be ignored during the initial peak detection routine, e.g., in FIG. 10, peak 1010 is the largest amplitude peak between bins of 2 and 250. The voltage range for identifying the peak can be established via empirical data from other sequencing chips.

In step 840, a first set of cells located within the single nanopore peak is determined. According to certain embodiments, step 840 can identify all cells having voltages within an identified width of the largest amplitude peak as the set of a single nanopore cells. The width parameter can be, e.g., the full width at half maximum, which can be used as a proxy for a standard deviation. In some embodiments, the width can be taken as a specified number of standard deviations, e.g., 2, 3, 4, etc. Measurements of local minima in the histogram could also be used. For example, a local minimum between the zero peak and the single nanopore peak can be used to determine a baseline for identifying the width of the single nanopore peak. Accordingly, embodiments can determine where the local maximum and minimum are within the histogram data. The integral, i.e., integrated area under histogram between the various local minimum can be used to identify the peak with the largest area, which would correspond to the single nanopore peak, under the assumption that this is the largest population for the chip as a whole.

It should be understood that the histogram peak corresponding to cells having a single nanopore need not be solely comprised of single nanopore cells to the exclusion of other types of cells. As shown in FIG. 10, the peak is not infinitely narrow and, as such, it is understood that while the population of cells within the peak will be dominated by single nanopore cells, some non-single nanopore cells may happen to have voltages that fall within the peak, depending on how the width of the peak is defined. According to certain embodiments, the width of the peak can be defined relative to the peak value, e.g., voltage cutoffs can be chosen to be where a level of the histogram is some specified fraction of a maximum value of the histogram peak (e.g., full width at half max, $1/e^2$, 99.9% level, etc.). Voltage cutoffs may be determined based on the minimum and maximum detections described above. Voltage values within the cutoffs define the set of cells that are to be considered single nanopore cells, where the number of non-single nanopore cells decreases as the width decreases. The placement of the cutoffs will involve a tradeoff between capturing a large fraction of the available single nanopore cells, while also excluding the majority of cells having something other than a single nanopore (e.g., zero nanopore cells, shorts, two or more nanopore cells, pseudo-pores cells, etc).

In the example shown in FIG. 10, cutoff 1010 is placed at 29 ADC counts and cutoff 1020 is placed at 115 ADC counts. In this example, cutoff 1010 eliminates most pseudo-pores and zero-pore cells (which have open channel voltages of less than 29 ADC counts), and likewise, cutoff 1020 eliminates most multi-pore and short circuited cells (which have open channel voltages of greater than 115 ADC counts). According to certain embodiments, to improve the accuracy of the chip, cells having voltages outside of the cutoffs may be deactivated or their outputs may be selectively removed or ignored. For example, after characterization, cells having a single nanopore may be effectively labeled by storing unique identifiers for each of these cells in memory. The during a sequencing operation, a processor may then activate only those pores that associated with a stored identifier. The converse is also possible, where cells to be deactivated are labeled with a unique identifier stored in memory.

In general, when determining the cutoffs using the histogram data, certain artifacts may be present that depend on the chosen location and width of the histogram bins. In some implementations of step 840, the set of single nanopore cells can be determined using a kernel density estimate (KDE) or other smoothing function to avoid and/or minimize histogram artifacts. In general, a KDE is used to estimate the underlying distribution function of a set of noisy data points. More specifically, a KDE process can build an estimated distribution function of the measured data from an admixture (or sum) of characteristic functions, one per measured data point. For example, a KDE may take as input the measured voltage data points, and for each voltage data point, compute the values of a continuous characteristic function (e.g. a Gaussian) with a location centered at the voltage value of that data point. This can be done for each data point, and the results can be summed to give the KDE of the underlying distribution function. Another way to visualize the KDE process is that to compute the KDE, the characteristic function (e.g., a Gaussian) is moved as a window function over the histogram, with the width of the window defined by the Gaussian width parameter. The choice of how to define the centers of each characteristic function is analogous to choosing the bin size for the histogram computation and will in general depend on the details of the data itself. In one implementation, the window is moved 0.2 of ADC value. In other embodiments, rather than using a uniform step for moving the characteristic function, the characteristic function can be computed with the center located at every measured voltage value in the measured data.

FIG. 11 shows a KDE of voltage values for different cells according to certain embodiments. The first peak 1101, which is small, corresponds to the cells with no nanopores. The second peak 1103 corresponds to the cells with one nanopore. The third peak 1105 and the fourth peak 1107 correspond to cells with two nanopores and three nanopores, respectively.

In step 850, a sequencing operation may be performed using only the identified single nanopore cells. The sequencing operation may proceed as described above in reference to FIG. 3.

Determining the set of single nanopore cells from a histogram (or distribution) of the measured open channel voltage data can be a robust process for identifying cells with a single nanopore because minimal assumptions may be made, as opposed to using fixed cutoff values. As the cells may vary from chip to chip and different biochemistry may be involved, such a robust process is desirable. For example, one may not know the exact value of the voltage for each single nanopore peak, and various nanopores may be used for different chips. Furthermore, the lipid bilayer can change over time. As the gain of a cell depends on both $R_{pore}$ and $C_{bilayer}$, a larger well or different solvent (or different annulus) can change gain, and therefore the open channel and threaded voltages.

V. Normalization

Once the usable cells of a chip are identified, a production mode can be run to sequence nucleic acids, one for each usable cell. The ADC values measured during sequencing can be normalized to provide greater accuracy. In some embodiments, the voltage level data that is acquired during a bright period of the AC drive voltage (referred to herein as the "bright mode voltages" or alternatively as the "bright period voltage") are normalized. For example, the bright mode voltages can be normalized by dividing each measured bright mode data point by the bright mode voltage of the cell when the nanopore is in an unthreaded state, referred to herein as the "open channel voltage" or "bright mode open-channel voltage." By normalizing the bright mode voltage level data, the dynamic range of the raw ADC measurements is rescaled to a normalized range, generally to provide a range between 0 and 1, although values greater than 1 are possible, depending on the specific value used for bright mode open-channel voltage.

Normalization can allow compensating for changes to the system, e.g., changes in the electrical properties of a sequencing cell. For instance, the capacitances of circuit 400 may change over time. For example, the capacitance of capacitor 426 ($C_{Bilayer}$) because of physical changes in the bilayer area or thickness, e.g., at the edges of a well, where such change is referred to as gain drift. As another example, charge can build up in the cell as a result of differences in charge transfer between bright periods and dark periods, which is referred to as baseline shift (and sometimes fast baseline shift). A slow baseline shift can be caused by variability in the measurements circuit and changes in the electrical properties of the bilayer membrane. These examples are described in more detail below.

Such changes can affect the values measured for the exact same state, thereby causing instabilities. However, normalization can compensate for such changes to provide normalized values (e.g., voltages or currents) that are stable over time, thereby allowing greater accuracy in determining the sequence of a nucleic acid.

A. Idealized Normalization

Figure 12A:
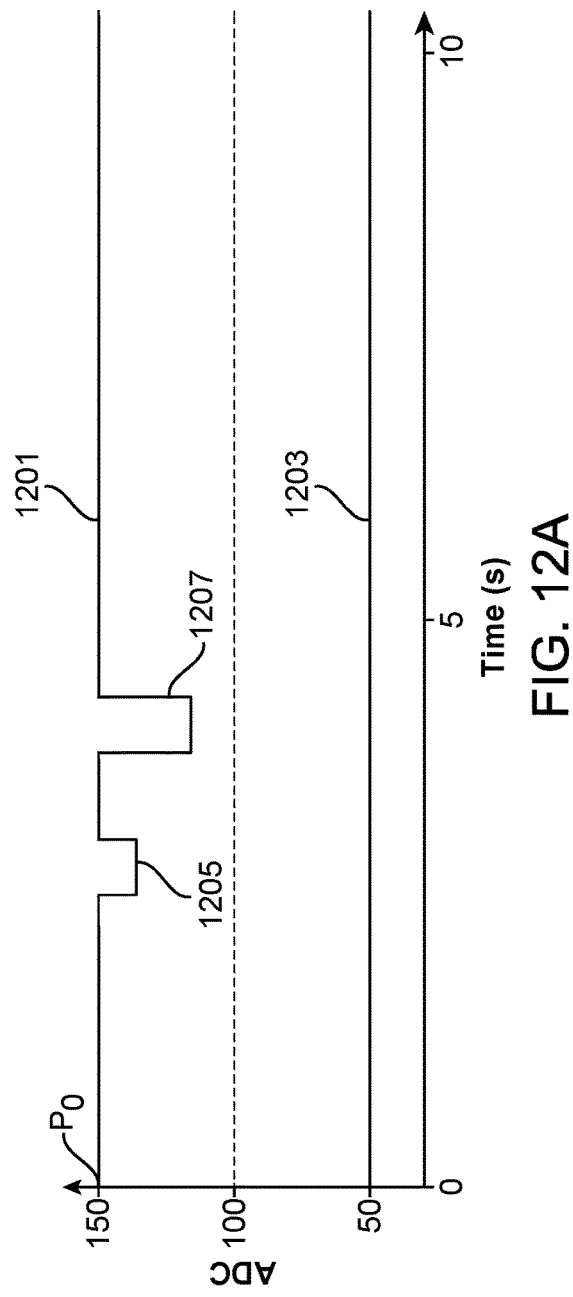
FIGS. 12A and 12B illustrates normalization of sequencing data, according to certain aspects of the present disclosure.
Figure 12B:
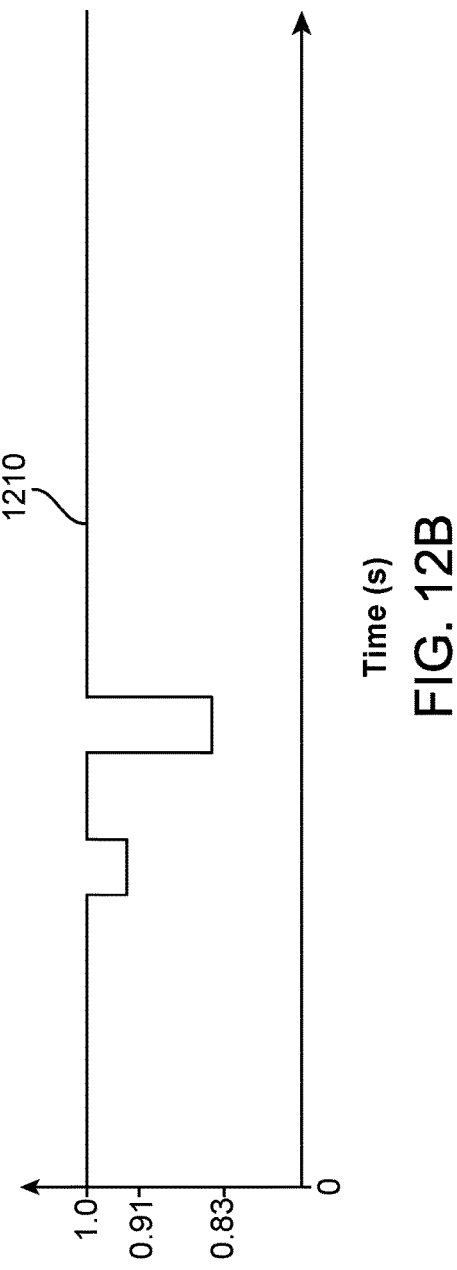

FIGS. 12A-12B illustrate the concept of normalization for an idealized ADC signal according to some embodiments. FIG. 12A shows idealized bright mode data 1201 and idealized dark mode data 1203 as might be measured by an ADC during a sequencing operation, e.g., as described above. The idealized ADC data of FIGS. 12A-12B is also shown on a much longer timescale than, e.g., the data described above in reference to FIG. 5. As such, the individual AC cycles are not visible, as is the case in FIG. 5. Nevertheless, it should be understood that bright mode data 1201 and dark mode data 1203 are acquired during different half cycles of the AC drive voltage $V_{liq}$. Furthermore, the data shown in FIG. 12A are idealized in the sense that no noise, gain drift, and/or baseline shift is present, i.e., the open channel voltages (both bright mode and dark mode) are constant over an individual AC cycle as well as constant over time. In addition, bright mode data 1201 shows threading events 1205 and 1207 that correspond to two separate hypothetical threading events of two different tagged nucleotides. The measured voltages at threading events 1205 and 1207 are different due to the different tagged nucleotides being threaded. As shown here, the threading events last over several AC cycles and occur on a fast enough timescale that during the threading events, no bright mode open-channel signal is measured.

In FIG. 12A, the open channel ADC value for the bright mode is represented by $P_0$, which may be used to normalize the ADC values for threading events 1205 and 1207. This normalization factor $P_0$ in this idealized example is constant at the measured value at t=0, which is 150 ADC values in this example. To perform the normalization in this case, all of the bright mode data can be divided by the same constant: $P_0$=150. For ease of description, the example of normalization by division is used throughout disclosure; however, one of ordinary skill will understand that multiplication by the inverse is mathematically equivalent and thus may also be used without departing from the scope of the present disclosure.

FIG. 12B shows the normalized bright mode data 1210 resulting from normalizing the idealized bright mode data 1201 of FIG. 12A. In the normalized bright mode data, the open-channel level and the tag levels are not the raw ADC values, but rather span the range from 0 to 1. Because the bright mode open channel voltage is constant in this case, the normalization factor $P_0$ can be used to normalize the entire signal across the entire duration of the sequencing run.

However, real signals suffer from a number of non-idealities that make this simple, single-valued normalization inaccurate. Two primary causes of errors in real sequencing systems are baseline shift and gain drift.

B. Gain Drift

Each sequencing cell has a voltage gain that depends on the lipid bi-layer capacitance. The gain corresponds to the voltage difference that is achieved between the pair of electrodes (e.g., counter electrode 210 and working electrode 202). For example, given the equation of C=q/V for a capacitor, as the capacitance increases, the voltage would decrease when a same amount of charge is present. Accordingly, if the lipid bi-layer capacitance changes over time, then the voltage gain changes over time. If the voltage gain changes over time, then the bright mode and dark mode (both open channel and threaded) can change over time. In any real system, the bilayer capacitance may change over time, e.g., as the bilayer deforms. Such changes typically occur on the timescale of hundreds or thousands of seconds and, though slower than a typical threading event, still should be accounted for if high accuracy measurements are desired.

Figure 13:
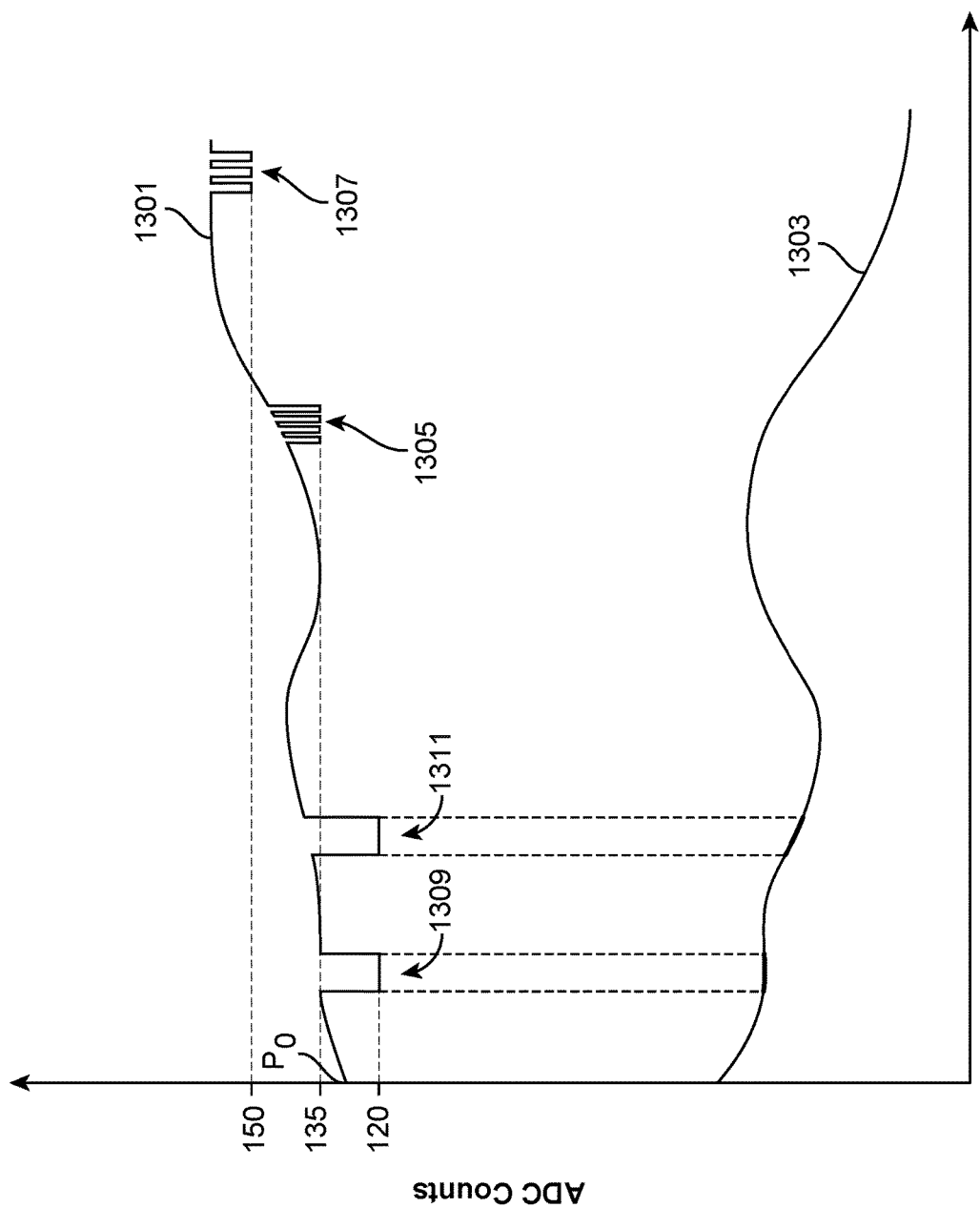
FIG. 13 illustrates gain drift according to certain aspects of the present disclosure.

FIG. 13 shows an idealized signal that suffers from gain drift (with non-realistic timescales for both threading events and non-realistic gain drift to allow for both phenomena to be clearly shown on the same graph). Like FIGS. 12A-12B, FIG. 13 shows an idealized bright mode data 1301 and idealized dark mode data 1303 as would be measured by an ADC during a sequencing operation. The gain drift is illustrated as the overall drift in the open channel voltages for both bright and dark modes, with the drift being anti-correlated between bright and dark modes (e.g., when the bright mode increases, the dark mode decreases and vice versa). For the sake of clarifying the effect that gain drift has on measured ADC level of the same tag over time, 4 threading events are also shown, with each threading event involving the same species of tag, resulting in a same drop in voltage from the current open channel voltage. However, despite the fact that the same tag is being threaded during each event, the ADC value of this tag drifts over time. Thus, it could be the case that for this cell, the same tag could be detected anywhere within a range of 120 to 150. As a result, non-normalized levels would be error prone.

To correct for the gain drift, a normalization procedure similar to that described above in reference to FIGS. 12A-12B may be performed. However, unlike the case in FIGS. 12A-12B, the open channel voltage in the bright mode is not constant over time, so the single value normalization described above (i.e., divide everything by $P_0$) fails to normalize the entire signal over time. Instead of the constant normalization, a more complex variable normalization can be applied, e.g., the normalization can be accomplished by dividing each raw bright-mode measured ADC value with an estimate of that point's open channel value. For each non-threaded region, an estimate of the open channel voltage can be made by any number of ways, e.g., by taking a local mean value or by using more sophisticated signal processing technique such as a Kalman filter, as described in more detail below. Thus, a local estimate can be obtained for the open channel value for the bright mode, so as to normalize a data point using the estimated voltage that is local to that data point.

On the other hand, the threaded regions of the signal can provide a challenge. For some threading events, there may be open channel data available if the threading rate is slow enough, e.g., as shown in threading events 1305 and 1307. When the threading rate is relatively slow, open channel values can be measured before the tag is threaded. Such open channel values can be measured for each cycle. This behavior is depicted in the comb-like lines shown for threading event 1305 and 1307. In these cases, the limited open channel data may be used to estimate the true open channel value during the threading event. This limited open channel data (i.e., limited relative to when no threading occurs) can be used to obtain a local estimate of the open channel value (e.g., local within time, so as to account for gain drift)

However, it may be the case that the threading is fast enough that no open channel data is captured in the bright mode, e.g., as shown for threading events 1309 and 1311. When the threading rate is sufficiently fast, the tag is immediately threaded, and no open channel values are measured. This lack of open channel voltages can be problematic when trying to determine a local estimate of the open channel; if there are not open channel values for a given time interval, no local estimate can be determined for that time interval. In these cases, it is possible to determine the local estimate for the open channel data in the bright mode using the dark mode data, as described in further detail below.

C. Baseline Shift

Baseline shift is a phenomenon that is related to charge imbalances that build up on certain elements (e.g., $C_{Double\ Layer}$) in the cell during the charging and discharging cycles that take place during the measurement process. For example, during the measurement process, excess charge can build up on the working electrode of the cell, represented by $C_{Double\ Layer}$ in FIG. 4. In one example, the charge imbalance is caused by the fact that both the nanopore and the tags have non-linear I-V characteristics. As a result of this nonlinearity, a charge and discharge cycle may not add or remove the same amount of charge to the capacitive elements. For example, negative and positive ions may not move from one electrode to the other electrode via the pore at the same rate over time, e.g., causing positive charge to build-up in the well. Note that the duty cycle can be 60% dark mode and 40% bright mode to address a typical difference in transmission rate of positive and negative ions, but when a rate changes, the duty cycle would have to change, which can be difficult to do.

As a result of this accumulated charge imbalance, the voltage measurements in a cell would increase (e.g., when positive charge builds up in the well). This shift in a baseline voltage can increase until it produces a voltage high enough to counterbalance the opposing voltage originally set up as a consequence of the charge imbalance. At which point, the charge can re-balance. Baseline shifts can occur in the both the dark mode and bright mode open channel states and in each of the four threaded states, with the magnitude and time constants for the shifts potentially being different in each of the open channel and four threaded states. As a result, the baseline shift can change in a generally random way that mirrors the stochastic binding events of the tags at the pore.

Figure 14:
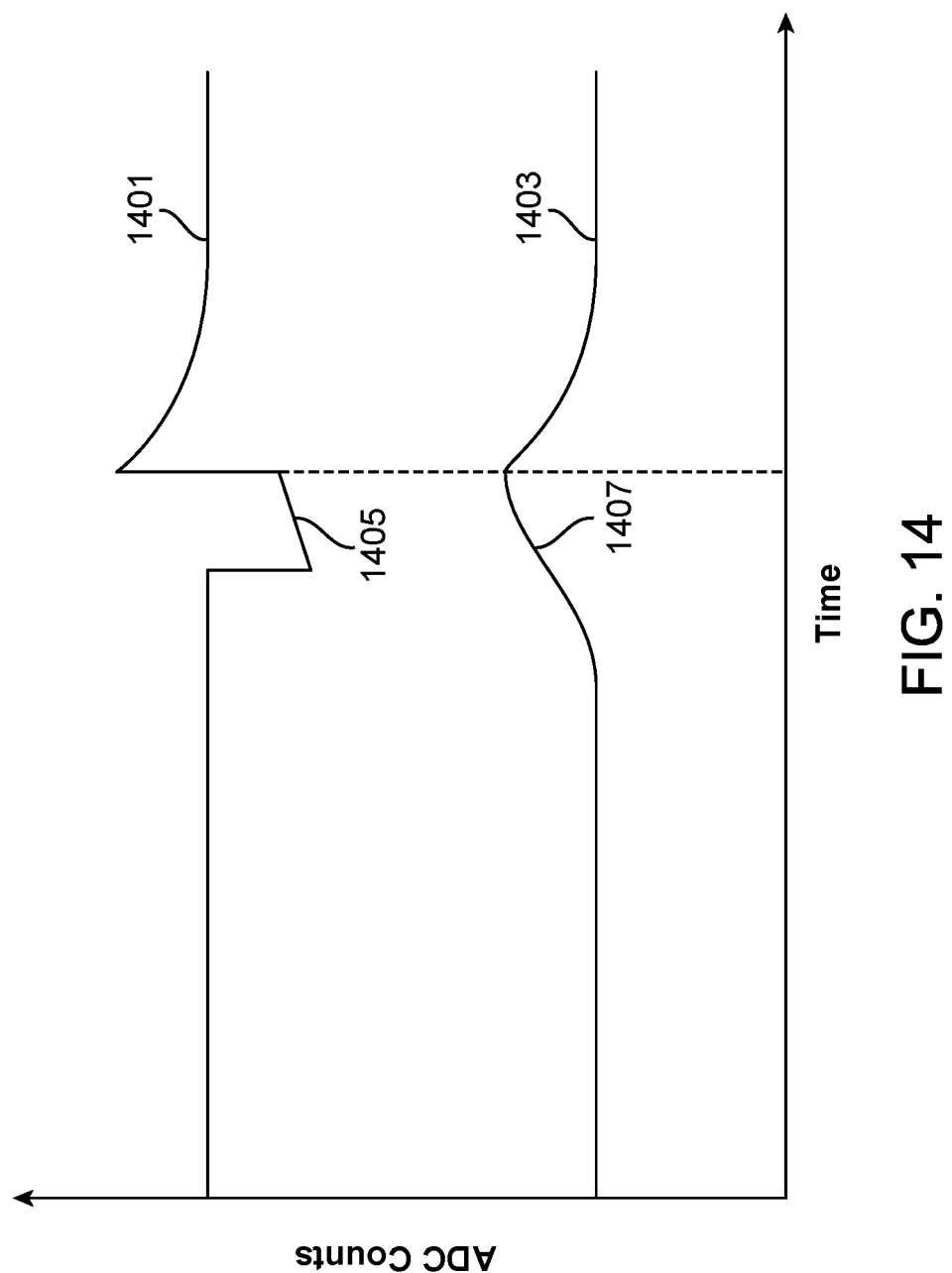
FIG. 14 illustrates baseline shift according to certain aspects of the present disclosure

FIG. 14 shows an idealized signal that exhibits baseline shift. Like FIGS. 12A-12B and FIG. 13, FIG. 14 shows an idealized bright mode data 1401 and idealized dark mode data 1403. This type of baseline shift generally occurs on a timescale that is on the order of the dwell time for a tag in a pore, a timescale that is generally much faster than the timescale for gain shift. Thus, gain shift is shown in FIG. 14.

Before a threading event 1410, the cell has reached equilibrium, i.e., the baseline voltage is what it needs to be to ensure equal charge transfer, e.g., to $C_{Double\ Layer}$ during the bright and dark modes. However, once the threading event 1410 begins, the system is driven out of equilibrium. More specifically, while effective resistance of the pore when the cell is in the dark mode stays the same, the effective resistance of the pore in the bright mode has increased. The increased resistance in the bright mode causes less charge to move during this mode, as compared to before the threading event occurred. Thus, a charge imbalance begins to form, which leads to an upward shifts 1405 and 1407 in both the tag level and the dark mode open channel level, respectively.

As with the gain shift phenomenon, to compensate for baseline shift, a variable, point-by-point normalization can be applied, e.g., the normalization can be accomplished by dividing each raw bright-mode measured ADC value with an estimate of that point's open channel value as described in further detail below. Such an estimate can be considered a local estimate as it is valid for a single point or a certain set of points within a time interval.

D. Other Offset Effects

There are various offset effects that can be accounted for in normalization without departing from the scope of the present disclosure. Some of these offset effects are described below 1. Intracycle Decay Cycle shape Ideally, the open channel voltage would be constant over a cycle in which no threading exists, and likewise the threaded voltages would be the same for a given bright mode cycle. Such constant behavior would provide a larger difference in the values for open channel versus the threaded voltages for different bases. Further, having constant behavior would allow easier discrimination between voltage levels. For instance, the peaks would be sharp in a histogram of the number of measured voltage values across a sequencing of a nucleic acid, as there would be less spread in values for open channel or any given threaded channel.

But, the measured voltage values during a cycle vary due to intracycle decay, as mentioned above. This intracycle decay is a result of the $C_{Double\ Layer}$ (capacitor 424 in FIG. 2) changing from one measurement to another during a cycle. This change in $C_{Double\ Layer}$ affects the decay rate of the voltage at the integrating capacitor so that the decay is slower for successive measurements, thereby resulting in slight changes in the measured ADC value.

To compensate for such changes, one could take just a single voltage reading, but that may not be as accurate as a multiple measurements. Some implementations can effectively get a single measurement by taking an average (mean) of the voltages over a given cycle. Such an average can be weighted based on a calculated or expected value for the intracycle decay rate. Such an average can be used as a measured ADC value, potentially where threaded voltage in a cycle can be given the value of the average.

2. Charge Injection Offset

An offset can also occur as a result of charge that is injected to circuit 400 via switch 401 of FIG. 4. Switch 401 is used for resetting the voltage on integrating capacitor 408 in order to take a new measurement using the ADC. Each time the switch closes, an amount of charge is injected into the circuit for that cell. For the charge injection, there is a transfer of certain number of electrons from a source to the drain, thereby dumping a certain amount of charge into the system. The charge distributes among the capacitors, which creates an offset. The offset would be acceptable if it was constant, but it is not constant.

Examples for why such a charge injection offset can vary are as follows. Over time, the surface area of the bilayer can become larger or smaller bilayer (e.g., by the annulus at the edges creeping in and out). This change can cause a ratio of the capacitance of the bilayer to change relative to the capacitance the integrating capacitance (e.g., 408). This ratio affects the time constant of the circuit, and thus what the measured voltage after a specific amount of time, as can be measured by the ADC. If the ratio is determined only once, this ratio value can be become outdated, and thus incorrect. Embodiments can use the magnitude of the charge injection, the capacitance of the bilayer, and how it is changing to determine a normalization to compensate for the charge injection offset.

Using FIG. 4 as an example, the switch 401 resets the voltage of the system, after which an ADC value is measured at a specified amount of time after the switch 401 is opened. The resetting and the measuring is repeated. As the switch is non-ideal, every time the switch 401 close, some charge is injected into the circuit. Charge builds up on $C_{bl}$ 426, thereby causing the baseline voltage to change as charge builds up on $C_{bl}$.

When the charge is injected, the charge is distributed in the circuit. The primary places are $C_{bl}$ 426 and integrating capacitor 408. The ratio of the charge between the two capacitors depends on the size of the bilayer. The offset of a particular cell changes over time, as the voltage changes on integrating capacitor 408. If the ratio stayed the same, then it would not change the measured offset, as it would stay the same over time. But, as $C_{bl}$ 426 changes, different amounts of charged will be injected to $C_{bl}$ 426 and integrating capacitor 408, thereby changing the offset. Such a problem would not exist if the capacitances did not change over time, as is typical for semiconductor capacitors, but is not true for biochemical elements that act as capacitors.

As a solution, $C_{bl}$ 426 can be measured over time. The capacitance of integrating capacitor 408 would not typically change over time, as it can be a semiconductor element. The charge can be quantified at the beginning of a sequencing run, and may be different for each cell. This charge can be determined as part of calibration, e.g., as part of determining VMzero. $C_{bl}$ 426 can be measured using the first point delta, which is the difference in the first voltages measured for bright and dark modes after a cycle switch in polarity, e.g., of a square wave. There is a relationship between the first point delta (FPD) and $C_{bl}$ 426. Such a relationship can be constant from cell to cell.

Accordingly, the change in FPD can be used to determine the change in the offset of VMzero. The relationship is based on the amount of charge injected into the system as measured for a beginning cycle, the value of integrating capacitor 408 for the cell, the initial measurement of $C_{bl}$ 426, and the change in FPD of the beginning cycle.

The following technique can be used to determine a change to VMzero as a result of the charge injection. The charge q=C*V, where q is charge, C is capacitance and V is voltage. C=$C_{bl}$ 426 +$C_{ncap}$ (integrating capacitor 408). V=q/($C_{bl}$+$C_{ncap}$), and the change in voltage due to a changing bilayer cap is: dV=q $(1/(C_{bl\_new}+C_{ncap})-1/(C_{bl\_old}+C_{ncap}))$. This change in voltage can be used to modify an ADC value before other normalization, e.g., to compensate for gain drift or baseline shift.

E. Hybrid-online Normalization Method

Figure 15:
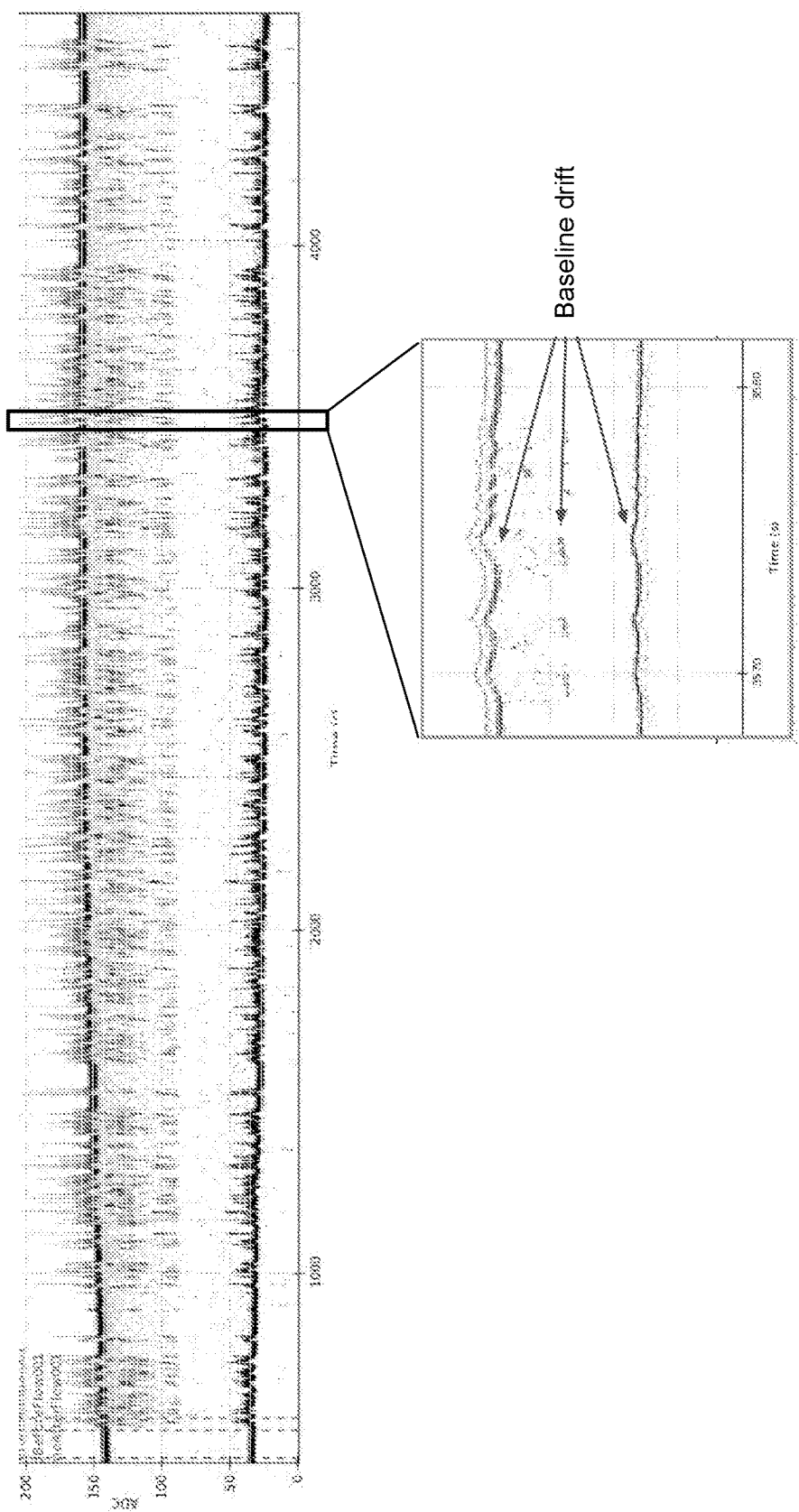
FIG. 15 shows sample data showing both gain drift and baseline shift according to certain aspects of the present disclosure.

While FIGS. 12-14 discussed gain drift and baseline shift as separate effects, these phenomena are likely to both occur together, likely with additional noise sources. For example, FIG. 15 shows test data from a sequencing cell at two different timescales showing both gain drift and baseline shift, as well as other more uniformly distributed but relatively fast random noise, e.g., noise that may originate from the ADC. In order to normalize the real signal shown in FIG. 11, the concepts from the description above can be unified into a single normalization method, referred to herein as the "hybrid-online" normalization method.

In an embodiment of such a hybrid-online technique, each bright mode value can be normalized by dividing that value by an estimate of the current (local) bright mode open channel value. Where possible, the estimate of the open channel value is determined from the bright mode data itself. However, in some cases, there is no bright mode open channel data; in that case, embodiments can infer the open channel value, e.g., compute the bright mode open channel level from the dark mode data in combination with an analytical model of the cell. This inferred bright mode open channel value can then be treated just like the values that are directly measured, and fed into a filtering process, e.g., a Kalman filter, to obtain the best estimate for the actual open channel value. The best local estimate can then be used to normalize the data.

Figure 16:
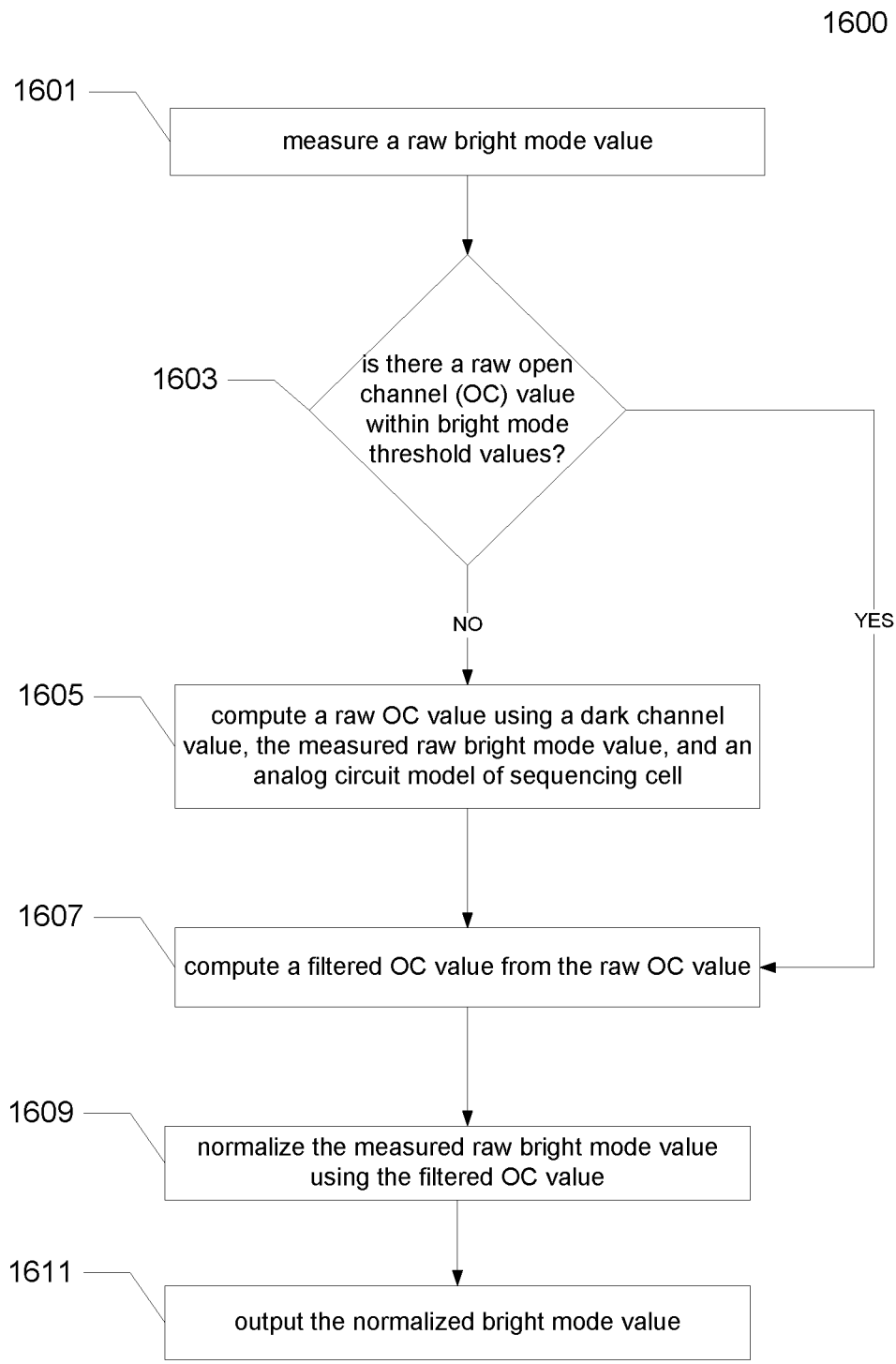
FIG. 16 is a flow chart illustrating an example method of normalization, according to certain aspects of the present disclosure.
Figure 17:
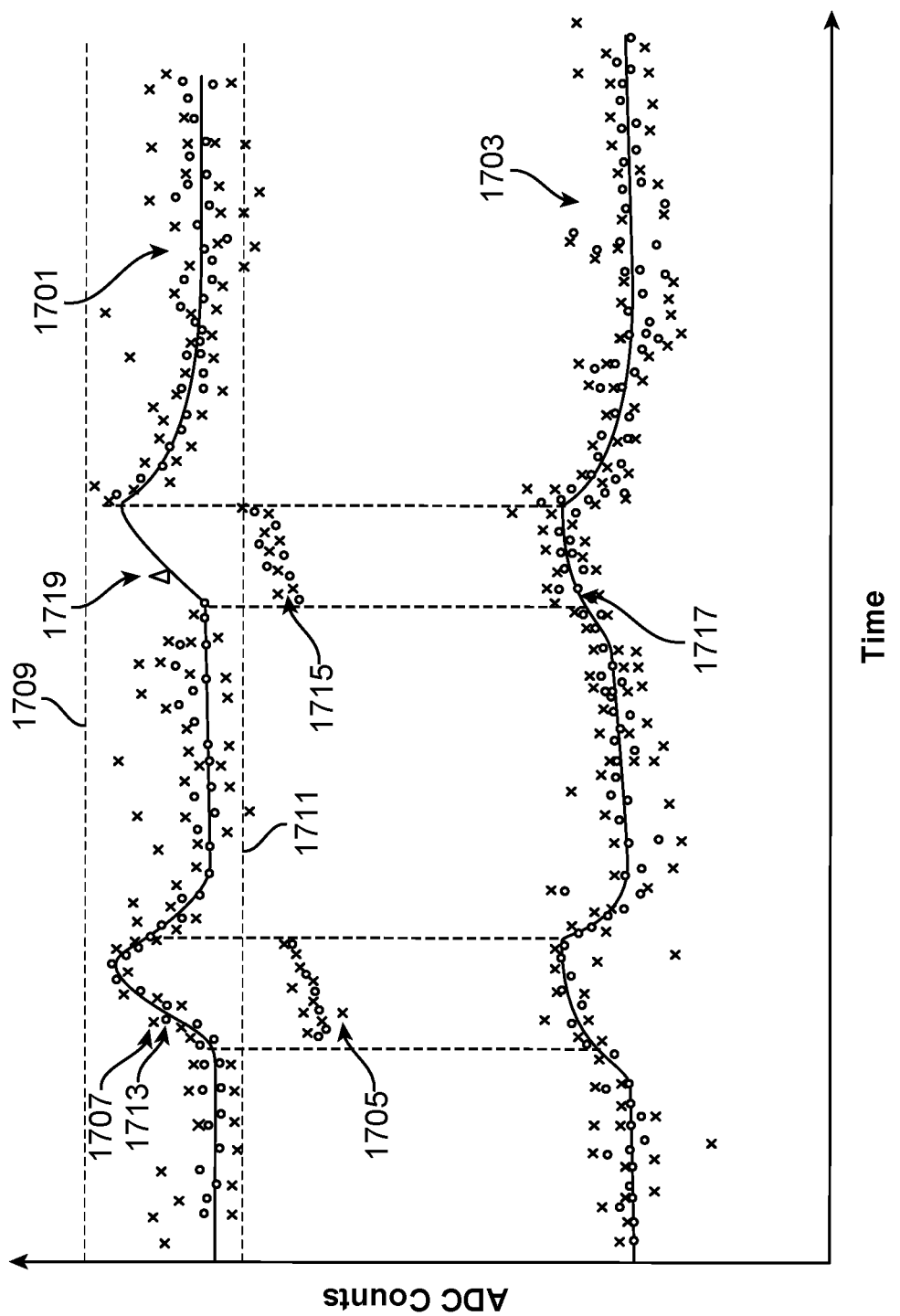
FIG. 17 shows sample data showing both gain drift and baseline shift according to certain aspects of the present disclosure.

FIG. 16 shows a flow chart for a hybrid-online normalization method according to one or more embodiments. FIG. 16 is described in relation to FIG. 17 and can be performed by a computer system, which may be connected with a sequencing device. FIG. 17 shows somewhat realistic sample data to aid in the description of the method. FIG. 17 is similar to the previous figures in that it includes idealized bright mode data 1701 and idealized dark mode data 1703, but also includes random noise. Data points represented by "x's" show the raw ADC values measured over time. Data points represented by circles show the filtered ADC data (also referred to herein as filtered signal values), e.g., circles show the output from a Kalman filter (or the like). Data points represented by triangles represent computed open channel data that is computed by the Kalman filter (or the like), but using the negative open channel signal, which may use an analytical system model, as will be described in further detail below. For reference, the straight lines represent the (unmeasurable) "ground truth" open channel values for both the bright and dark modes.

In step 1601 a raw bright mode data point is measured, e.g., raw bright mode value 1605 shown in FIG. 17. According to some embodiments, this data point is measured by an ADC and sent to a digital processor, e.g., ADC 410 and digital processor 430, respectively, as shown in FIG. 4. The digital processor can be part of a computer system that includes other components. In this example, raw bright mode value 1705 occurs during a threading event and is therefore systematically lower than the open channel data points.

In step 1603, the digital processor tests to see if there are any bright mode raw open channel (OC) values that correspond to the measured bright mode value 1705. Whether a bright mode OC value corresponds can be determined based on a timing threshold, e.g., whether the two values are within a specific time interval. The criterion of a time interval can ensure that the estimate is local in time, and therefore an accurate estimate. The length of the time interval can vary based on the time scale(s) of the offset(s) that are being compensated. In some embodiments, a sufficient number of OC values satisfying the timing threshold can be required, e.g., using a count threshold.

If there is one or more bright mode raw OC values that do correspond to a current raw bright mode value (e.g., 1705), the bright mode raw OC values can be filtered. In this example, the threading rate associated with this particular threading event is slow enough that indeed there is a bright mode raw OC value, e.g., data point 1707. Note that in this example, due to the phenomena of baseline shift, both the OC values and the threaded values are trending upward as the cell attempts to settle to a new equilibrium value. Some embodiments may restrict the range of ADC values for which OC data can be found to only data points within a range between and upper threshold 1709 and a lower threshold 1711. The particular values for upper threshold 1709 and lower threshold 1711 can be chosen so that the range of values straddles the expected range of values for the bright mode OC values so that the filtering process does not inadvertently select a threaded value as an OC value.

Because there does exist a bright mode OC value, the method proceeds to step 1607 for computing a filtered OC value from the raw OC value. One purpose of applying a filter to the raw data in step 1607 is to more accurately estimate a true open channel value from the selected raw open channel value. The filter may be a discrete recursive filter such as a Kalman filter, as described in more detail below. The filter can take as input a bright mode raw OC value (e.g., data point 1707) and output a filtered OC value 1713 that is closer to the ground truth OC value. In FIG. 17, the set of filtered OC values are represented by circles. And, as can be seen form the comparing the raw data to the filtered data, the variance of the filtered data is lower than the raw data. Thus, the filter can act as a type of low pass filter in this instance.

In step 1609, the measured bright mode value 1705 is then normalized using the filtered OC value 1713, e.g., by dividing measured bright mode value 1705 by filtered OC value 1713.

In step 1611, the normalized bright mode value (not shown) is then output and or stored in memory to be later used during a base calling process.

Returning to the first step in the method shown in FIG. 16, an alternative case where no bright mode OC data is available will now be described.

In step 1601, a raw bright mode value is measured, e.g., raw bright mode value 1715 shown in FIG. 17. In this example, raw bright mode value 1715 occurs during a threading event and is thus, systematically lower than the open channel data points.

In step 1603, a computer system can test to see if there are any bright mode raw OC value(s) that corresponds to the measured bright mode value 1715; if present, the raw OC value(s) are selected to be filtered. In this example, the threading rate associate with this particular threading event is fast enough that there is no corresponding bright mode raw OC value. Accordingly, the method proceeds to step 1605.

In step 1605, the computer system computes an estimate of the bright mode raw OC value using a dark channel value, e.g., dark channel value 1717. In some embodiments, the dark channel value can be used as the bright mode raw OC value. In various embodiments, the dark channel value may be a filtered dark channel value (e.g., that has already been computed using a filter running separately on values of the dark channel data) or may be a raw dark channel value.

In some implementations, the computation of the estimate can use an analytical model of the cell circuit, e.g., as shown in FIG. 4, to compute the estimate of the bright mode raw OC value. Such an analytical model can be used when two offsets act in a different manner, e.g., multiplicative in magnitude (e.g., gain drift) and a common shift (baseline shift). For example, let $P_t$ correspond to the open channel bright value at a given time t, and let $P_0$ represent an initial value of the bright channel. Likewise, let $N_t$ represent the dark channel value at time t and let $N_0$ represent an initial value of the dark channel. The model then includes the following system of linear equations:

$$P(t)=m*(1+b*c)*P_0 \quad (1)$$

$$N(t)=m*(1-b)*N_0, \quad (2)$$

where m is the gain drift, b is the baseline shift, and c is the baseline shift ratio between the bright channel and the dark channel, $P_0$ and $N_0$ are initial bright channel and dark channel values, respectively, and P(t) and N(t) are subsequent (at some later time t) bright channel and dark channel values. In principle, the system of equations (1)-(2) is an over-determined one. There are 2*N number of equations with N being the number of data points acquired in the bright and dark channels; stated another way, Equations (1) and (2) are defined for each measured data point. Accordingly, all unknown constants can be solved if there are a sufficient number of data points measured. In practice, the value of c can be determined empirically, e.g., in an offline manner using the whole dataset, while the values of b and m can be computed online (e.g., as the data is being parsed from beginning to end), one b and m being computed for each of the measured data points.

With knowledge of c and either b or m, Equations (1) and (2) can be combined to provide a closed form solution for the current bright mode open channel value $P_t$ as a function of the dark channel data $N_t$ and $N_0$ and the initial bright channel value $P_0$. Accordingly, in step 1005 the $P_t$ serves as the estimate for the raw bright mode OC value, even when no bright mode data exists because the threading rate is too fast. As gain drift m changes slower than baseline shift b, values for P(t) and N(t) can be used to compute m and b. Then, at a later time, when a P(t) is not available, the previously computed gain drift m can be used. In some embodiments, gain drift m and baseline shift b can be filtered (e.g., moving averages of them) and then used to determine P(t). Thus, step 1605 can involve a corresponding bright mode OC value and a corresponding dark mode OC value.

In step 1607, the raw OC value computed from Equations (1)-(2) is then filtered like a directly measured OC value, i.e., it is passed to a filter to then compute a filtered OC value that is an improved estimate for the actual OC value absent measurement noise. FIG. 17 shows one example of a filtered OC value 1719 (shown as an open triangle) that has been computed using dark channel value 1717 in combination with the model of Equations (1)-(2).

Steps 1609 and 1611 proceed in a manner identical to the case when actual bright mode OC data is available and directly measured. More specifically, for this example, in step 1609 the measured bright mode value 1715 is normalized to the filtered OC value 1719, e.g., by dividing measured bright mode value 1715 by filtered OC value 1719.

In step 1611, the normalized bright mode value (not shown) is then output and or stored in memory to be later used during a base calling process.

In the example method shown in FIG. 16, and as described in further detail below in reference to Eqns. (7)-(8), some embodiments may employ a single channel filter (single-channel in the sense that the filter model is a one dimensional model of P(t)). In these embodiments, the output of the filter is a single value representing the best estimate of the bright mode open channel value, P(t). All other values are either obtained directly from the measured data (bright and dark mode) and/or computed from the model represented by Eqns. (1) and (2) using the measured data as input to the model.

Other methods of employing filtering may be employed without departing from the scope of the present disclosure. For example, in some embodiments, a multi-channel filter may be employed (e.g., an "extended Kalman filter") and one or more of P(t), N(t), m(t), and b(t) may be tracked and filtered by separate filter channels as described in further detail below in reference to Eqn. (9). In some embodiments, the filter may include additional channels to track all four bright mode threaded values in addition to P(t), N(t), m(t), and/or b(t).

F. Kalman Filter for Computing Filtered Open Channel Values

A Kalman filter is a Bayesian estimator. There is some prior probability that corresponds to the believed system state, some observation, and some weighting between the two based on the confidence in the two. It is an iterative process in that for every observation there is an update of the estimate of the state, and update the estimate of the uncertainty in that state. More specifically the Kalman algorithm comprises two main steps: a "predict" step and a "correct" step. In the "predict" step, the new state of the system and new error covariance of the data is predicted based on the prior values according to the following equations:

$$\hat{x}_k^- = A\hat{x}_{k-1} + Bu_{k-1} \quad (3)$$

$$P_k^- = AP_{k-1}A^T + Q, \quad (4)$$

where equation 2 describes how to predict a new a priori state estimate $\hat{x}_k^-$ from the state at a previous time step $\hat{x}_{k-1}$ and where Equation 3 describes how to predict a new a priori estimate for the error covariance from the error covariance at the previous time step. Once the new a priori estimates for the process state and covariance are obtained, these values are "corrected" based on information obtained by the actual measurement of the process state. The "correction" step proceeds according to the following equations:

$$K_k = P_k^- H^T (HP_k^- H^T + R)^{-1} \quad (5)$$

$$\hat{x}_k = \hat{x}_k^- + K_k(z_k - H\hat{x}_k^-) \quad (6)$$

$$P_k = (1 - K_k H)P_k^- \quad (7)$$

In the "correction" step, the first thing that is done is to compute the so-called Kalman gain K. Next, the process is measured to obtain the actual state measurement $z_k$. Next, the a posteriori state estimate $\hat{x}_k$ is computed from the previously computed a priori state estimate $\hat{x}_k^-$ by incorporating the measurement $z_k$ as shown in Equation (6). Finally, the a posteriori error covariance estimate $P_k$ is computed from the previously computed a priori state estimate error covariance estimate $P_k^-$ according to Equation (7). These new estimates are then fed back into another "predict" step at the next time step and the procedure continues recursively as more data comes in.

Because of its discrete, recursive nature, the Kalman filter does not require large amounts of data, but can just look at one piece of data at a time. It is good for a stream of data, and can work with GPUs, as GPUs cannot hold a large section of data trace in memory. This is unlike low pass filter or Fourier transform where all the data is needed in memory.

In various embodiments, either a Kalman filter or an nonlinear extension of the Kalman filter known as the Extended Kalman filter may be employed to provide estimates for either the dark mode values or the bright mode open channel values. For the case of the linear Kalman filter, the model for the bright mode and/or dark mode open channel values is a constant, one dimensional process, i.e., $$\hat{x}_t = P_{OC}(t) = C \quad (8)$$

$$P_t \geq P_k(t) \quad (9)$$

where C is a constant.

For the extended Kalman filter, the process is modeled according to the following three dimensional vector:

$$\hat{x}_t = \begin{bmatrix} P_{OC}(t) \\ N_{OC}(t) \\ b(t) \end{bmatrix} \quad (10)$$

where $P_{OC}(t) = P_{OC}^{k+}(1+cb)$, $N_{OC}(t) = N_{OC}^{k-}(1-b)$, $b(t) = B$, and where B a constant, b is the baseline shift, and c is the baseline shift ratio between the positive cycle and the negative cycle. According to this embodiment, f is an empirically determined constant and $P_{OC}^{k+}$ and $N_{OC}^{k-}$ are the Kalman predictions of the open channel levels in the bright and dark modes, respectively. Embodiments that employ an extended Kalman filter may be beneficial if the various processes being modeled (e.g., the bright mode open channel voltage $P_{OC}$, the dark mode open channel voltage $N_{OC}$, and baseline drift b) are independent and/or vary according to different timescales.

G. Method Using Dark Channel to Normalize Threaded Voltages

As exampled above, an open channel voltage may not always be available. In such circumstances, an open channel dark voltage may be used.

Figure 18:
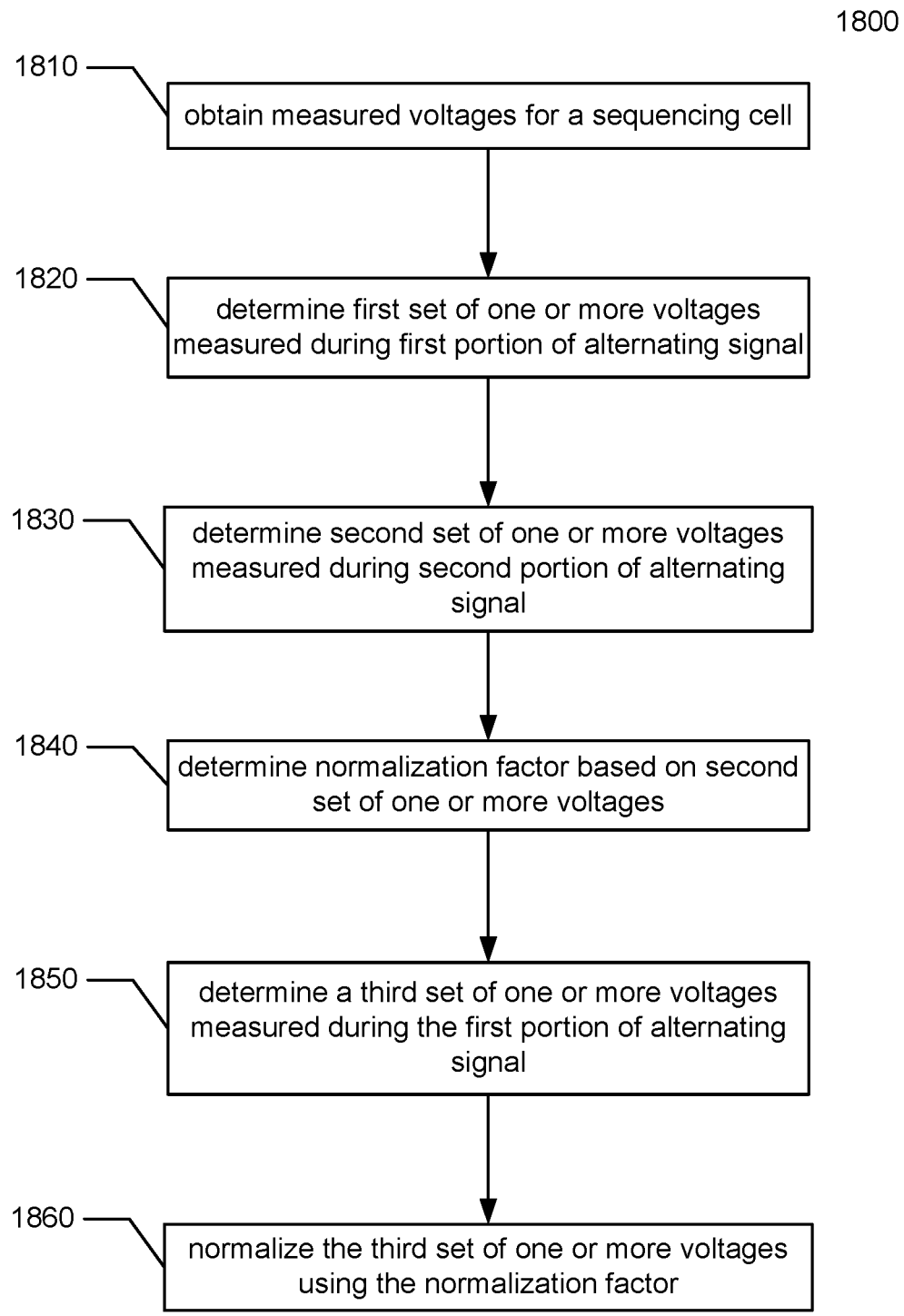
FIG. 18 is a flow chart illustrating an example method of normalization, according to certain aspects of the present disclosure.

FIG. 18 shows a flow chart for a normalization method using open channel dark period voltages according to one or more embodiments. FIG. 18 can be performed by a computer system, which may be connected with a sequencing device, e.g., as described above in reference to FIGS. 1-4.

In step 1810, a plurality of measured voltages are obtained for a sequencing cell. For example, during the measurement, a voltage can be applied across the sequencing cell, which includes a nucleic acid. The applied voltage may be an alternating signal, e.g., an AC signal having a first portion (e.g., a bright period, also referred to herein as a "bright phase") and a second portion (e.g., a dark period, also referred to herein as a "dark phase") relative to a reference voltage. According to certain embodiments, the reference voltage may be a reference voltage (e.g., $V_{PRE}$ 405 in FIG. 4) that is applied to an integrating capacitor, e.g., $n_{cap}$, as shown in FIG. 4. According to some embodiments, voltages can be measured by an ADC and sent to a digital processor, e.g., ADC 410 and digital processor 430, respectively, as shown in FIG. 4. The digital processor can be part of a computer system that includes other components. The voltages may also be obtained by receiving the voltages at a processor of a computer system.

In step 1820, a first set of one or more voltages measured in step 1810 during the first portion of the alternating signal is determined, e.g., one or more voltages measured during the bright period of the alternating signal are selected by the digital processor 430. The first set of voltages may correspond to various bright periods. Such measurements can occur as described herein and can occur at various times of sequencing different parts of a nucleic acid of a given cell.

In step 1830, a second set of one or more voltages measured during the second portion of the alternating signal is determined. For example, the second set of one or more voltages can be measured during the dark period of the alternating signal in step 1810 and can be selected by the digital processor 430. The second set of one or more voltages can be measured across various dark periods. According to certain embodiments, the first set of one or more voltages and second set of one or more voltages are determined with no molecule in a nanopore of the sequencing cell, i.e., when the cell is in an open channel state. These voltages are referred to herein as open channel voltages, as described in more detail above in reference to FIGS. 3-5.

In step 1840, a normalization factor is determined based on the second set of one or more voltages, i.e., the normalization factor is determined based on the measured one or more dark period voltages. According to certain embodiments, the normalization factor may be a bright period open channel value computed using Eqns (1) and (2) based on the one or more dark period voltages, e.g., as described above in reference to FIG. 16, and in particular in accordance with the model described in step 1605. In some embodiments, the normalization factor can be the one or more dark period voltages themselves. Like the method described above in reference to FIG. 16, the normalization factor (and indeed any of the measured or computed values) may be filtered, e.g., using a discrete recursive filter, or the like.

In step 1850, a third set of one or more voltages measured during the first portion of the alternating signal is determined. According to certain embodiments, the third set of one or more voltages may be measured when a tag molecule is threaded in the nanopore of the sequencing cell, the tag molecule corresponding to a particular nucleotide. Examples of the third set of voltages are often referred to herein as bright mode threaded voltages. The third set of one or more voltages may be measured across various bright periods.

In step 1860, the third set of one or more voltages is normalized using the normalization factor. As described above in reference to FIG. 16, the normalization may be a computed (i.e., estimated) open channel voltage and the normalization is accomplished by dividing by the computed open channel voltage. Alternatively, the normalization may be accomplished by a division by the reciprocal of the computed open channel voltage.

The normalized voltages can be used to determine a sequence of the nucleic acid. The normalization allows voltage levels corresponding to different tags to be consistent over time, and thus allowing bases to be accurately determined.

H. Method Compensating for Gain Drift and Baseline Shift

Figure 19:
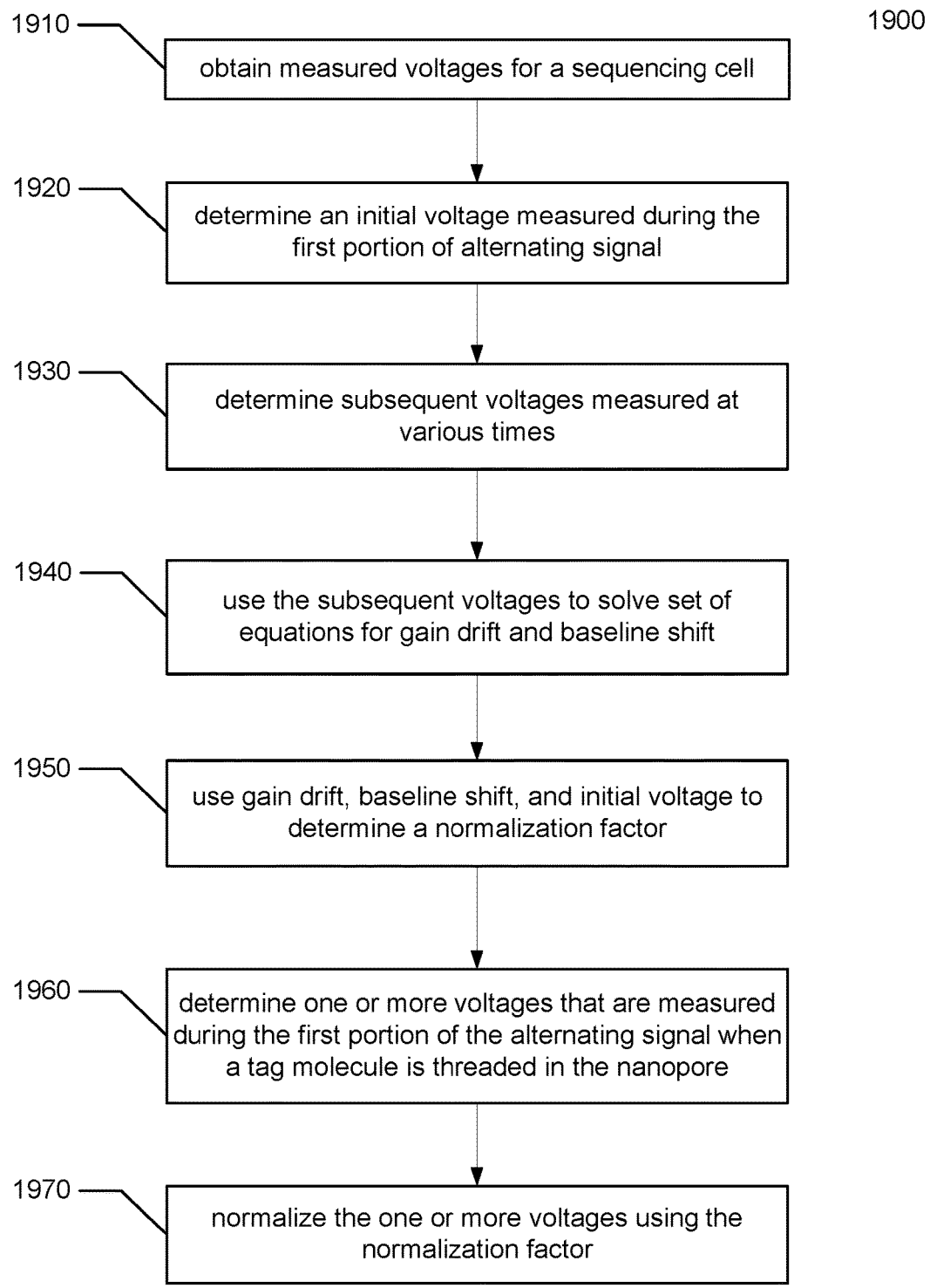
FIG. 19 is a flow chart illustrating an example method of normalization, according to certain aspects of the present disclosure.

FIG. 19 shows a flow chart for a normalization method compensating for gain drift and baseline shift according to one or more embodiments.

In step 1910, a set of measured voltages is obtained for a sequencing cell in a manner similar to that described above in reference to FIGS. 16 and 18.

In step 1920, an initial voltage measured during the first portion of the alternating signal is determined. According to certain embodiments, the first portion of the alternating signal can be the bright period (or bright phase) of the alternating signal as described above in reference to FIGS. 16 and 18. The initial voltage is initial as it comes before later measured voltages, and does not imply that it is a very first voltage to be measured in time.

In step 1930, subsequent voltages measured at various times are determined. For example, subsequent voltages can be measured during one or more bright and or dark periods of the alternating signal, during one or more cycles of the AC signal.

In step 1940, the subsequent voltages are used to solve a set of equations for a gain drift m and a baseline shift b. For example, Eqns. (1) and (2) described above may be used.

According to certain embodiments, the gain drift m can result from a capacitance of a circuit of the sequencing cell changing over time, and the baseline shift b can result from an accumulation of charge of the circuit of the sequencing cell over time. As shown by Eqns. (1) and (2) above, each value of the subsequent voltages can be defined as including the gain drift m and the baseline shift b.

In step 1950, the gain drift m, the baseline shift b, and the initial voltage are used to determine a normalization factor. According to certain embodiments, the normalization factor may be a computed, i.e., estimated, bright mode open channel voltage that results from a model like that described in Eqns. (1)-(2).

In step 1960, one or more voltages are determined, where these voltages are measured during the first portion of the alternating signal when a tag molecule is threaded in the nanopore of the sequencing cell, the tag molecule corresponding to a particular nucleotide. These one or more voltages determined at this step are also referred to herein as bright channel threaded voltages.

In step 1970, the one or more voltages are normalized using the normalization factor.

The normalization is accomplished in the same manner described above in reference to FIGS. 16 and 18. The normalized voltages can then be used to determine a sequence of a nucleic acid being sequenced in a given cell.

Like the method described above in reference to FIG. 16, the methods described in FIGS. 18-19 can normalize a sequencing signal without requiring any measured bright mode open channel data and thus can result in an improved sequencing system that can produce more robust and accurate sequences. To accomplish the normalization, embodiments can estimate the open channel voltage to be used for normalization from the data that is available, potentially just dark mode open channel voltages. According to certain embodiments, the estimate may be made by a digital processor that takes measured dark mode voltages as input into a model that predicts what the corresponding open channel voltage would be based on the model of the cell, e.g., Eqns (1)-(2) described above. Accordingly, embodiments can allow for improved normalization of the signal in cases where there is fast threading and no bright mode open channel data available.

While the methods described above, e.g., in reference to FIGS. 6-8, 16, 18, and 19, relate to calibration and/or normalization of signal values that represent voltages, other types of signals are possible and thus other types of signal values may be processed without departing from the scope of the present disclosure. For example, the circuitry of a cell may be configured such that signal values represent measurements of voltages, currents, or any other quantity (e.g., time) that may be used to derive the voltage and/or current at any point in a circuit of the sequencing cell.

I. Summary

As discussed above, a new P(t) and N(t) may be determined for each cycle. For each switch to modulate the voltage to be positive (break period), a new P(t) can be determined, e.g., at 80 Hz. In some embodiments, using data points from the bright and the dark modes as independent observations helps to provide greater accuracy in the normalization. Additionally, during threading events, the dark mode can act as a built-in calibration source because the threading events have unknown voltage levels, and thus are difficult to use for normalization.

Normalization can be performed point-by-point as data arrives, e.g., the normalization may be done point-by-point in near real time by a digital processor, e.g., digital processor 430 shown in FIG. 4. As described above in reference to FIGS. 6-8, point-by-point normalization is beneficial for signals with time-varying drifts because a different normalization factor can be determined for each data point, e.g., normalization factor can change depending on the measured gain drift and the baseline shift. Likewise, a new charge injection offset can also be determined for each cycle. Alternatively, each data point to be normalized can be an average of individual measurements in a cycle, e.g., an average of points over a time window.

As to filtering embodiments, it is possible to determine the baseline shift b and gain drift m through a deconvolution process that employs both the bright mode data and dark mode data. However, if there is fast threading, then there may not be many bright mode open channel data points and thus a reliable deconvolution cannot be performed. For example, fast threading might occur immediately when the bright mode begins. Then there would only be the threaded data and no open channel data. Furthermore, it may take 100 cycles for the tag to be catalyzed to the nucleic acid strand, and thus bright mode open channel data will be missing for these 100 cycles (which amounts to more than 1 s if missing bright mode data for an 80 Hz cycle frequency). Accordingly, gain drift and baseline shift could be difficult to track with just the threaded channel. In some embodiments, the hybrid online normalization method provides an improved normalization technique when open channel data is simply not reliably available in the bright mode. As described above, the hybrid online technique leverages information from the dark mode to provide a measurement of the open channel value in the bright mode, e.g., by leveraging the model of Eqns. (1) and (2) above. In other words, even during a series of fast threading events, the method can estimate what an open channel value would have been in the absence of a tag in the nanopore.

In some embodiments, the hybrid online normalization technique can be employed without using any additional filtering or signal processing techniques (such as Kalman filtering or the like). In this case, Eqns. (1)-(2) can be solved using an estimate of P/P0 from a previous cycle, with the initial values of: P/P0=1, m=1, and b=0. Using these initial values and the new measurements of P(t) and N(t), Eqns. (1)-(2) can be solved to obtain the new estimate for the values measured at the cycle. However, such a solution just provides a comparison of the current open channel value to the initial one and may be prone to error. Such a solution does not leverage the information from previous cycles to determine a stable normalization factor. In addition, such a solution does not leverage the correlation between the positive and negative channels.

As an improved technique, it is beneficial to employ an estimation filter (e.g. a Kalman filter or the like) that leverages historical information (the measurement values themselves in addition to the their respective noise distributions) to determine an improved normalization factor at each cycle, while also not having to analyze all of the data collectively. Accordingly, such a technique is beneficial because it fully leverages all available information to make more accurate estimates of the raw measured data and also does not require all of the raw data to be stored in memory, thereby loosening the hardware requirements for practical implementation. With respect to leveraging prior knowledge of the accuracy/noise of historical measurements, for example, embodiments can determine values for b and m and also their respective confidence values. In addition, for each new data point, new updated estimates for b and m and their respective new confidence values can be determined.

When obtaining updated estimates for b and m, the confidence values can then be used to indicate how much to weight the new values for b and m when computing updated estimates, e.g., when combining the new values with the previous value to obtain the updated estimates that more closely match the ground truth.

Thus, in some embodiments, a current state (P, N, b and/or m) can be determined and, as the system evolves in time, new measurements of the state can be made as well as new measurements of the uncertainty associated with the measurements of the new state. If the measurements are not very certain, then the estimated value (i.e. the value output from the estimation filter, e.g., the Kalman filter) of the new state will be dominated by the value of the current state (i.e., when combining the old and new measurements to get the estimate of the new state, the weight for the new measurement will be small compared to the previous measurement). Likewise, the updates of b and m can be performed separately, with each having a current state (and measurement of that current state) and a new state (and a measurement of that new state). In some embodiments, the new measurement can be determined by solving Eqns. (1)-(2). In some implementations, the uncertainty for the current state can be determined from how m is changing, e.g., by determining a variance of m values. In other implementations, the uncertainty into the new observation can be specified as a constant, empirical parameter (e.g., 0.03). Further for the current state, one can see how the new measurement is different than the current state, and that difference can be used to determine the uncertainty over time. More measurements should provide more certainty, as for standard error of the mean.

In some embodiments, a threading voltage could be used instead of or in addition to N. The use of both open channel voltages and one or more threaded voltages can provide an overdetermined system. One could identify a voltage range corresponding to a particular tag, so that only one positive channel is used. Another way is to have a weighting matrix, such that all threaded voltages are used, but the solution can be weighted toward the tag for which the voltage is expected to correspond. In one embodiment, if a threaded channel is observed and no positive open channel is observed, one can ignore the gain drift (e.g., set at the previous value) and solve for b, e.g., using just the dark mode. Since the gain moves at a slower timeline, such a treatment can be justified.

VI. Determining Bases

After normalization, embodiments can determine clusters of voltages for the threaded channels, and use the clusters to determine cutoff voltages for discriminating between different bases. In some embodiments, a Laplacian mixture model can be used. The width for the Laplacian can be determined as part of the fitting procedure. There can be 5 Laplacian functions, one for positive open channel and one for each of the four nucleotides. The clusters can be determined per cell.

With a stable chip, the levels could be stable across cells and chips. Even so, monitoring can still be performed. The clustering can be done at the end, or updated as new data is determined for a sequencing run.

The baseline shift b can be used in other contexts, e.g., in later parts of the pipeline. For example, information can be used about the signal through time, and information about each unique pore and sensor complex. For instance, b is function of t, as a second order signal of what was threaded and how long was it threaded for. This can be used for polishing information for basecalling.

The normalization can be used to feed two estimates about the reliability of the base call. To get an estimate of the uncertainty from the Kalman filter, the uncertainty can be used to adjust the Q score. Thus, the uncertainty can be used as an input parameter to the determination of the Q score. The uncertainty can be viewed as how well did the normalization work.

VII. Computer System

Figure 20:
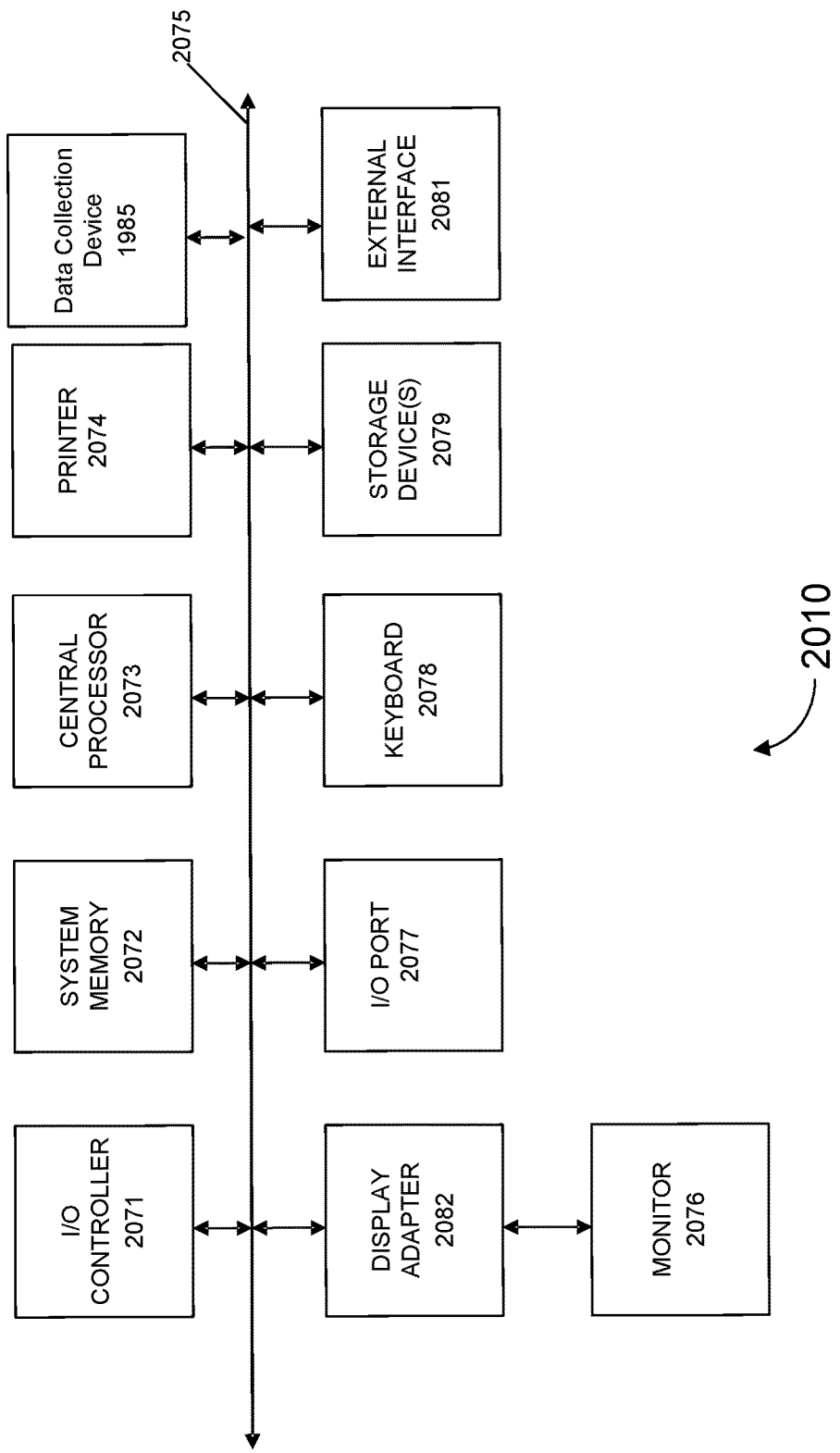
FIG. 20 is a computer system, according to certain aspects of the present disclosure.

Any of the computer systems mentioned herein may utilize any suitable number of subsystems. Examples of such subsystems are shown in FIG. 20 in computer system 2010. In some embodiments, a computer system includes a single computer apparatus, where the subsystems can be the components of the computer apparatus. In other embodiments, a computer system can include multiple computer apparatuses, each being a subsystem, with internal components. A computer system can include desktop and laptop computers, tablets, mobile phones and other mobile devices.

The subsystems shown in FIG. 20 are interconnected via a system bus 2075. Additional subsystems such as a printer 2074, keyboard 2078, storage device(s) 2079, monitor 2076, which is coupled to display adapter 2082, and others are shown. Peripherals and input/output (I/O) devices, which couple to I/O controller 2071, can be connected to the computer system by any number of means known in the art such as input/output (I/O) port 2077 (e.g., USB, FireWire®). For example, I/O port 2077 or external interface 2081 (e.g. Ethernet, Wi-Fi, etc.) can be used to connect computer system 2010 to a wide area network such as the Internet, a mouse input device, or a scanner. The interconnection via system bus 2075 allows the central processor 2073 to communicate with each subsystem and to control the execution of a plurality of instructions from system memory 2072 or the storage device(s) 2079 (e.g., a fixed disk, such as a hard drive, or optical disk), as well as the exchange of information between subsystems. The system memory 2072 and/or the storage device(s) 2079 may embody a computer readable medium. Another subsystem is a data collection device 85, such as a camera, microphone, accelerometer, and the like. Any of the data mentioned herein can be output from one component to another component and can be output to the user.

A computer system can include a plurality of the same components or subsystems, e.g., connected together by external interface 2081 or by an internal interface. In some embodiments, computer systems, subsystem, or apparatuses can communicate over a network. In such instances, one computer can be considered a client and another computer a server, where each can be part of a same computer system. A client and a server can each include multiple systems, subsystems, or components.

Aspects of embodiments can be implemented in the form of control logic using hardware (e.g. an application specific integrated circuit or field programmable gate array) and/or using computer software with a generally programmable processor in a modular or integrated manner. As used herein, a processor includes a single-core processor, multi-core processor on a same integrated chip, or multiple processing units on a single circuit board or networked. Based on the disclosure and teachings provided herein, a person of ordinary skill in the art will know and appreciate other ways and/or methods to implement embodiments of the present invention using hardware and a combination of hardware and software.

Any of the software components or functions described in this application may be implemented as software code to be executed by a processor using any suitable computer language such as, for example, Java, C, C++, C#, Objective-C, Swift, or scripting language such as Perl or Python using, for example, conventional or object-oriented techniques. The software code may be stored as a series of instructions or commands on a computer readable medium for storage and/or transmission. A suitable non-transitory computer readable medium can include random access memory (RAM), a read only memory (ROM), a magnetic medium such as a hard-drive or a floppy disk, or an optical medium such as a compact disk (CD) or DVD (digital versatile disk), flash memory, and the like. The computer readable medium may be any combination of such storage or transmission devices.

Such programs may also be encoded and transmitted using carrier signals adapted for transmission via wired, optical, and/or wireless networks conforming to a variety of protocols, including the Internet. As such, a computer readable medium may be created using a data signal encoded with such programs. Computer readable media encoded with the program code may be packaged with a compatible device or provided separately from other devices (e.g., via Internet download). Any such computer readable medium may reside on or within a single computer product (e.g. a hard drive, a CD, or an entire computer system), and may be present on or within different computer products within a system or network. A computer system may include a monitor, printer, or other suitable display for providing any of the results mentioned herein to a user.

Any of the methods described herein may be totally or partially performed with a computer system including one or more processors, which can be configured to perform the steps. Thus, embodiments can be directed to computer systems configured to perform the steps of any of the methods described herein, potentially with different components performing a respective steps or a respective group of steps. Although presented as numbered steps, steps of methods herein can be performed at a same time or in a different order. Additionally, portions of these steps may be used with portions of other steps from other methods. Also, all or portions of a step may be optional. Additionally, any of the steps of any of the methods can be performed with modules, units, circuits, or other means for performing these steps.

The specific details of particular embodiments may be combined in any suitable manner without departing from the spirit and scope of embodiments of the invention. However, other embodiments of the invention may be directed to specific embodiments relating to each individual aspect, or specific combinations of these individual aspects.

The above description of example embodiments of the invention has been presented for the purposes of illustration and description. It is not intended to be exhaustive or to limit the invention to the precise form described, and many modifications and variations are possible in light of the teaching above.

A recitation of "a", "an" or "the" is intended to mean "one or more" unless specifically indicated to the contrary. The use of "or" is intended to mean an "inclusive or," and not an "exclusive or" unless specifically indicated to the contrary. Reference to a "first" component does not necessarily require that a second component be provided. Moreover reference to a "first" or a "second" component does not limit the referenced component to a particular location unless expressly stated.

All patents, patent applications, publications, and descriptions mentioned herein are incorporated by reference in their entirety for all purposes. None is admitted to be prior art.

What is claimed is:

1. A method of using a sequencing cell, the method comprising:
obtaining a plurality of measured signal values for the sequencing cell having a voltage applied across the sequencing cell, the sequencing cell including a nucleic acid, wherein the applied voltage includes an alternating signal having a first portion and a second portion relative to a reference voltage;
determining a first set of one or more signal values measured during the first portion of the alternating signal;
determining a second set of one or more signal values measured during the second portion of the alternating signal, wherein the first set of one or more signal values and second set of one or more signal values are determined with no molecule in a nanopore of the sequencing cell;
determining a normalization factor based on the second set of one or more signal values;
determining a third set of one or more signal values measured during the first portion of the alternating signal when a tag molecule is threaded in the nanopore of the sequencing cell, the tag molecule corresponding to a particular nucleotide; and
normalizing the third set of one or more signal values using the normalization factor to obtain one or more normalized signal values.

2. The method of claim 1, wherein each of the plurality of measured signal values corresponds to a voltage or a current of the sequencing cell as measured at a particular time.

3. The method of claim 1, wherein the normalization factor accounts for gain drift resulting from a capacitance of a circuit of the sequencing cell changing over time.

4. The method of claim 1, wherein the normalization factor accounts for a baseline shift resulting from an accumulation of charge of a circuit of the sequencing cell over time.

5. The method of claim 1, wherein an absolute value of a difference of one of the second set of one or more signal values and the reference voltage is used to determine the normalization factor.

6. The method of claim 1, further comprising:
filtering the second set of one or more signal values to obtain one or more filtered signal values; and
using the one or more filtered signal values to determine the normalization factor.

7. The method of claim 1, wherein filtering the second set of one or more signal values uses a Kalman filter.

8. The method of claim 1, wherein obtaining the plurality of measured signal values for the sequencing cell includes:
charging a capacitive element of a circuit of the sequencing cell, wherein the nanopore comprises a resistive element of the circuit;
partially discharging the capacitive element for a specified amount of time or to a specified voltage level; and
measuring a voltage at a point in the circuit after the specified amount of time or measuring a duration of time required for the point on the circuit to reach the specified voltage level.

9. The method of claim 1, wherein obtaining the plurality of measured signal values for the sequencing cell includes:
charging a capacitive element of a circuit of the sequencing cell, wherein the nanopore comprises a resistive element of the circuit;
partially discharging the capacitive element for a specific amount of time or to a specified current level; and
measuring a current in the circuit after the specified amount of time or measuring a duration of time required for a current at a point on the circuit to reach the specified current level.

10. The method of claim 8, wherein the first portion of the alternating signal includes a plurality of sub-periods of cycles during which a voltage between a first electrode and a second electrode of the sequencing cell is such that the tag molecule may be forced into the nanopore.

11. The method of claim 10, wherein the alternating signal is applied to the first electrode, wherein the second electrode is at the reference voltage, and wherein the capacitive element is charged to be at the reference voltage.

12. The method of claim 1, further comprising:
determining the normalization factor also based on the first set of one or more signal values.

13. The method of claim 1, wherein determining the normalization factor based on the second set of one or more signal values includes:
determining a second voltage value that approximates a first open-channel voltage value that would occur during the first portion of the alternating signal, the determining of the second voltage value using a baseline shift computed using the second set of one or more signal values; and
using the second voltage value as the normalization factor or using the second voltage value and other voltage values to determine an average voltage value that is used as the normalization factor.

14. The method of claim 1, further comprising:
determining a sequence of the nucleic acid using the one or more normalized signal values.

15. A method of using a sequencing cell, the method comprising:
obtaining a plurality of measured signal values for the sequencing cell having a voltage applied across the sequencing cell, the sequencing cell including a nucleic acid, wherein the applied voltage includes an alternating signal having a first portion and a second portion relative to a reference voltage;
determining an initial signal value measured during the first portion of the alternating signal;
determining subsequent signal values measured at various times;
using the subsequent signal values to solve a set of equations for a gain drift m and a baseline shift b, the gain drift m resulting from a capacitance of a circuit of the sequencing cell changing over time, and the baseline shift b resulting from an accumulation of charge of the circuit of the sequencing cell over time, wherein each value of the subsequent signal values is defined as including the gain drift m and the baseline shift b;
using the gain drift m, the baseline shift b, and the initial signal value to determine a normalization factor;
determining one or more signal values measured during the first portion of the alternating signal when a tag molecule is threaded in a nanopore of the sequencing cell, the tag molecule corresponding to a particular nucleotide; and
normalizing the one or more signal values using the normalization factor.

16. The method of claim 15, wherein the set of equations comprises a model that relates one or more first measured signal values measured during the first portion of the alternating signal to one or more second measured signal values measured during the second portion the alternating signal.

17. The method of claim 15, further comprising:
determining an initial signal value measured during the second portion of the alternating signal; and
using the gain drift m, the baseline shift b, the initial signal value measured during the second portion of the alternating signal, and the initial signal value measured during the first portion of the alternating signal to determine a normalization factor.

18. The method of claim 16, wherein the model comprises a linear system of equations comprising the following:

$$P(t)=m*(1+b*c)*P0$$

$$N(t)=m*(1-b)*N0$$

where m is the gain drift, b is the baseline shift, and c is a baseline shift ratio between signal values measured the first portion and the second portion,
wherein P0 is the initial signal value measured during the first portion of the alternating signal and N0 is an initial signal value measured during the second portion of the alternating signal, and
wherein P(t) is a subsequent signal value measured during the first portion and N(t) is a subsequent signal value measured during the second portion.

19. The method of claim 16, wherein, during a time when a tag molecule is threaded in the nanopore of the sequencing cell, the normalization factor is computed to be an estimated value of a signal value that would have occurred in absence of the tag molecule being threaded in the nanopore.

20. The method of claim 15, wherein each of the plurality of measured signal values corresponds to a voltage or a current of the sequencing cell as measured at a particular time.

21. A system comprising:
a sequencing cell that includes a nanopore, the nanopore configured to receive a tag that is connected to a nucleotide, thereby creating a threading event;
a signal generator that applies an alternating signal across the nanopore of the sequencing cell, each cycle of the alternating signal comprising a first portion and a second portion, wherein voltage levels of the second portion are opposite of a reference voltage than voltage levels of the first portion;
an analog-to-digital converter that acquires a plurality of measured signal values from the sequencing cell; and
a digital processor configured to:
determine a first set of one or more signal values measured during the first portion of the alternating signal;
determine a second set of one or more signal values measured during the second portion of the alternating signal, wherein the first set of one or more signal values and second set of one or more signal values are determined with no molecule in the nanopore of the sequencing cell;
determine a normalization factor based on the second set of one or more signal values;
determine a third set of one or more signal values measured during the first portion of the alternating signal when a tag molecule is threaded in the nanopore of the sequencing cell, the tag molecule corresponding to a particular nucleotide; and
normalize the third set of one or more signal values using the normalization factor to obtain one or more normalized signal values.

* * * * *